US010272180B2

(12) United States Patent
Jiang et al.

(10) Patent No.: US 10,272,180 B2
(45) Date of Patent: Apr. 30, 2019

(54) FUNCTIONALIZED ZWITTERIONIC AND MIXED CHARGE POLYMERS, RELATED HYDROGELS, AND METHODS FOR THEIR USE

(71) Applicant: University of Washington, Seattle, WA (US)

(72) Inventors: Shaoyi Jiang, Redmond, WA (US); Tao Bai, Seattle, WA (US); Harihara Subramanian Sundaram, Seattle, WA (US); Andrew William Sinclair, Seattle, WA (US); Jean-René Ella-Menye, Seattle, WA (US); Priyesh Jain, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 15/509,607

(22) PCT Filed: Sep. 9, 2015

(86) PCT No.: PCT/US2015/049197
§ 371 (c)(1),
(2) Date: Mar. 8, 2017

(87) PCT Pub. No.: WO2016/040489
PCT Pub. Date: Mar. 17, 2016

(65) Prior Publication Data
US 2017/0266350 A1    Sep. 21, 2017

Related U.S. Application Data

(60) Provisional application No. 62/048,155, filed on Sep. 9, 2014.

(51) Int. Cl.
| | | |
|---|---|---|
| A61L 27/52 | (2006.01) | |
| C08G 81/02 | (2006.01) | |
| A61F 2/00 | (2006.01) | |
| A61K 9/00 | (2006.01) | |
| A61L 15/24 | (2006.01) | |
| A61L 31/14 | (2006.01) | |
| A61L 15/22 | (2006.01) | |
| A61L 15/42 | (2006.01) | |
| A61L 24/00 | (2006.01) | |
| A61L 24/04 | (2006.01) | |
| A61L 27/16 | (2006.01) | |
| A61L 27/38 | (2006.01) | |
| A61L 31/06 | (2006.01) | |
| A61L 31/10 | (2006.01) | |
| C08F 220/36 | (2006.01) | |
| C12N 5/00 | (2006.01) | |
| A61K 47/58 | (2017.01) | |

(52) U.S. Cl.
CPC ............ *A61L 27/52* (2013.01); *A61K 9/0024* (2013.01); *A61K 47/58* (2017.08); *A61L 15/22* (2013.01); *A61L 15/24* (2013.01); *A61L 15/42* (2013.01); *A61L 24/0031* (2013.01); *A61L 24/046* (2013.01); *A61L 27/16* (2013.01); *A61L 27/3804* (2013.01); *A61L 31/06* (2013.01); *A61L 31/10* (2013.01); *A61L 31/145* (2013.01); *C08F 220/36* (2013.01); *C08G 81/021* (2013.01); *C12N 5/0018* (2013.01); *C08F 2220/365* (2013.01); *C12N 2533/30* (2013.01); *C12N 2539/00* (2013.01)

(58) Field of Classification Search
CPC .......... A61L 27/52; A61L 15/22; A61L 15/24; A61L 15/42; A61L 24/0031; A61L 24/046; A61L 27/16; A61L 27/3804; A61L 31/06; A61L 31/10; A61K 47/58
See application file for complete search history.

(56) References Cited

U.S. PATENT DOCUMENTS

| | | |
|---|---|---|
| 8,822,213 B2 | 9/2014 | Stayton et al. |
| 2010/0152708 A1 | 6/2010 | Li et al. |
| 2010/0249267 A1 | 9/2010 | Jiang et al. |
| 2011/0097277 A1 | 4/2011 | Jiang et al. |
| 2011/0123621 A1 | 5/2011 | St. John et al. |
| 2011/0195104 A1* | 8/2011 | Jiang et al. |
| 2011/0319569 A1 | 12/2011 | Emrick et al. |
| 2012/0322939 A1* | 12/2012 | Jiang et al. |

FOREIGN PATENT DOCUMENTS

| | | |
|---|---|---|
| CA | 2 825 024 A1 | 8/2012 |
| WO | 2010/096422 A1 | 8/2010 |
| WO | 2011/057219 A2 | 5/2011 |

(Continued)

OTHER PUBLICATIONS

International Preliminary Report on Patentability dated Mar. 14, 2017, issued in corresponding International Application No. PCT/US2015/049197, filed Sep. 9, 2015, 12 pages.
International Search Report and Written Opinion dated Dec. 14, 2015, issued in corresponding International Application No. PCT/US2015/049197, filed Sep. 9, 2015, 14 pages.
Georgiou, T.K., and C.S. Patrickios, "Synthesis, Characterization, and DNA Adsorption Studies of Ampholytic Model Conetworks Based on Cross-Linked Star Copolymers," Biomacromolecules 9(2):574-582, Dec. 2007.

(Continued)

*Primary Examiner* — Alma Pipic
(74) *Attorney, Agent, or Firm* — Christensen O'Connor Johnson Kindness PLLC

(57) ABSTRACT

Functionalized zwitterionic and mixed charge polymers and copolymers, methods for making the polymers and copolymers, hydrogels prepared from the functionalized zwitterionic and mixed charge polymers and copolymers, methods for making and using the hydrogels, and zwitterionic and mixed charge polymers and copolymers for administration for therapeutic agents.

35 Claims, 12 Drawing Sheets

(56) References Cited

FOREIGN PATENT DOCUMENTS

| WO | 2011/057224 A2 | 5/2011 |
|---|---|---|
| WO | 2011/156590 A3 | 12/2011 |

OTHER PUBLICATIONS

Li, L., et al., "Synthesis and Characterization of Dendritic Star-Shaped Zwitterionic Polymers as Novel Anticancer Drug Delivery Carriers," Journal of Biomaterials Science, Polymer Edition 25(14-15):1641-1657, Jul. 2014.
First Office Action dated Apr. 4, 2018, issued in corresponding Chinese Application No. 20150058874.5, filed Sep. 9, 2015, 13 pages.
Extended European Search Report dated May 7, 2018, issued in corresponding European Application No. 15840077.0, filed Sep. 9, 2015, 8 pages.
Berkes, C.A., and S.J. Tapscott, "MyoD and the Transcriptional Control of Myogenesisin," Seminars in Cell & Developmental Biology 16(4-5):585-595, Aug.-Oct. 2005.
Cao, J., et al., "Cellular Internalization of Doxorubicin Loaded Star-Shaped Micelles With Hydrophilic Zwitterionic Sulfobetaine Segments," Biomaterials 35(15):4517-4524, May 2014.
Cao, J., et al., "Novel pH-Sensitive Micelles Generated by Star-Shape Copolymers Containing Zwitterionic Sulfobetaine for Efficient Cellular Internalization," Journal of Biomedical Nanotechnology 9(11):1847-1861, Nov. 2013.
Chamberlain, J.R., et al., "Gene Targeting in Stem Cells From Individuals With Osteogenesis Imperfecta," Science 303(5661):1198-1201, Feb. 2004.
Elmasri, H., et al., "Fatty Acid Binding Protein 4 is a Target of VEGF and a Regulator of Cell Proliferation in Endothelial Cells," FASEB Journal 23(11):3865-3873, Nov. 2009.
Goldberg, I.J., "Lipoprotein Lipase and Lipolysis: Central Roles in Lipoprotein Metabolism and Atherogenesis," Journal of Lipid Research 37(4):693-707, Apr. 1996.
Hisamatsu, Y., et al., "A Supramolecular Gel From a Quadruple Zwitterion That Responds to Both Acid and Base," Angewandte Chemie International Edition 52(48):12550-12554, Nov. 2013.
Jaiswal, R.K, et al., "Adult Human Mesenchymal Stem Cell Differentiation to the Osteogenic or Adipogenic Lineage is Regulated by Mitogen-Activated Protein Kinase," Journal of Biological Chemistry 275(13):9645-9652, Mar. 2000.
Katsetos, C.D., et al., "Class III Beta-Tubulin in Human Development and Cancer," Cell Motility and the Cytoskeleton 55(2):77-96, Jun. 2003.
Khoo, M.L., et al., "Long-Term Serial Passage and Neuronal Differentiation Capability of Human Bone Marrow Mesenchymal Stem Cells," Stem Cells and Development 17(5):883-896, Oct. 2008.
Kiani, C., et al., "Structure and Function of Aggrecan," Cell Research 12(1):19-32, Mar. 2002.
Lee, H.J., et al., "Enhanced Chondrogenesis of Mesenchymal Stem Cells in Collagen Mimetic Peptide-Mediated Microenvironment," Tissue Engineering: Part A 14(11):1843-1851, Nov. 2008.
Li, W.-J., et al., "Multilineage Differentiation of Human Mesenchymal Stem Cells in a Three-Dimensional Nanofibrous Scaffold," Biomaterials 26(25):5158-5166, Sep. 2005.
Li, Y., et al., "Mobility of Lysozyme Inside Oxidized Starch Polymer Microgels," Soft Matter 7(5):1926-1935, Mar. 2011.
Lin, W., et al., "Biocompatible Long-Circulating Star Carboxybetaine Polymers," Journal of Materials Chemistry B 3:440-448, Jan. 2015.
Liu, P.-S., et al., "Surface Modification of Cellulose Membranes With Zwitterionic Polymers for Resistance to Protein Adsorption and Platelet Adhesion," Journal of Membrane Science 350(1-2):387-394, Mar. 2010.
Mountaintop Medical, LLC, "The Market for Advanced Drug Delivery Systems," Kalorama Information, Dec. 2010, 178 pages.
Mwale, F., et al., "The Effect of Glow Discharge Plasma Surface Modification of Polymers on the Osteogenic Differentiation of Committed Human Mesenchymal Stem Cells," Biomaterials 27(10)2258-2264, Apr. 2006.
Nakamura, A., et al., "Osteocalcin Secretion as an Early Marker of In Vitro Osteogenic Differentiation of Rat Mesenchymal Stem Cells," Tissue Engineering, Part C: Methods 15(2)169-180, Jun. 2009.
Nedvídková, J., et al., "Adiponectin, an Adipocyte-Derived Protein," Physiological Research 54(2):133-140,2005.
Nguyen, A.T., et al., "Stable Protein-Repellent Zwitterionic Polymer Brushes Grafted From Silicon Nitride," Langmuir 27(6):2587-2594, Mar. 2011.
Saussede-Aim, J., et al., "Vinorelbine Induces Beta3-Tubulin Gene Expression Through an AP-1 Site," Anticancer Research 29(8):3003-3009, Aug. 2009.
Sila-Asna, M., et al., "Osteoblast Differentiation and Bone Formation Gene Expression in Strontium-Inducing Bone Marrow Mesenchymal Stem Cell," Kobe Journal of Medical Sciences 53(1-2):25-35, 2007.
Smith, J., "Advanced Polymers for Medical Applications," Kalorama Information, Feb. 2002, 310 pages.
Wang, X., et al., "Synthesis of Biomimetic Hyperbranched Zwitterionic Polymers as Targeting Drug Delivery Carriers," Journal of Applied Polymer Science 128(5):3289-3294, Jun. 2013.
Williams, C.G., et al., "In Vitro Chondrogenesis of Bone Marrow-Derived Mesenchymal Stem Cells in a Photopolymerizing Hydrogel," Tissue Engineering 9(4):679-688, Aug. 2003.
Zhang, F., et al., "Active Tissue-Specific DNA Demethylation Conferred by Somatic Cell Nuclei in Stable Heterokaryons," Proceedings of the National Academy of Scienses of the USA (PNAS) 104(11):4395-4400, Mar. 2007.
Zhang, Z., et al., "Surface Grafted Sulfobetaine Polymers via Atom Transfer Radical Polymerization as Superlow Fouling Coatings," Journal of Physical Chemistry B 110(22):10799-10804, Jun. 2006.
Zhao, J., et al., "Improved Biocompatibility and Antifouling Property of Polypropylene Non-Woven Fabric Membrane by Surface Grafting Zwitterionic Polymer," Journal of Membrane Science 369(1-2):5-12, Mar. 2011.

* cited by examiner

+

FUNCTIONALIZED ZWITTERIONIC AND MIXED CHARGE POLYMERS, RELATED HYDROGELS, AND METHODS FOR THEIR USE

CROSS-REFERENCE TO RELATED APPLICATION

This application claims the benefit of U.S. Patent Application No. 62/048,155, filed Sep. 9, 2014, expressly incorporated herein by reference in its entirety.

STATEMENT OF GOVERNMENT LICENSE RIGHTS

This invention was made with Government support under Contract Nos. DMR 1307375 and CBET-1264477, awarded by the National Science Foundation, and under Contract Nos. N00014-14-1-0090 and N00014-15-1-2277 awarded by the Office of Naval Research. The Government has certain rights in the invention.

BACKGROUND OF THE INVENTION

Hydrogels have long been of interest for biological and biomaterial applications due to their high water content that mimics the interstitial tissue environment, ensures high diffusive permeability, and provides biomimetic mechanical strengths. Particular interest has been given to PEG hydrogels and poly(2-hydroxyethyl methacrylate) (pHEMA) hydrogels because, in addition to the general properties of hydrogels, they are also commonly considered to be low fouling, bioinert, and versatile.

pHEMA hydrogels have found use in and been studied for applications such as contact lenses, artificial cornea, drug delivery vehicles, cartilage substitutes, and tissue scaffolds, among others. The hydration of pHEMA, however, is lower than that of native tissue, and its fouling, while low, is higher than other nonfouling materials. Furthermore, pHEMA functionalization via the hydroxyl group is generally difficult.

PEG hydrogels are routinely used, and can only be modified for applications that require a bioinert background with specific added bioactive functionalities for controlled in vitro and in vivo uses when additional functional groups are introduced into PEG hydrogels. However, it has been found that PEG is susceptible to oxidation. The susceptibility of PEG to oxidative damage reduces its utility for applications that require long-term material stability. For applications in which maximal biological stability and nonfouling are required, however, PEG-based materials are insufficient.

Recently, zwitterionic compounds, including poly(carboxybetaine methacrylate), have been demonstrated to be ultra-low-fouling, meaning that surfaces coated with these polymers allow less than 5 ng/cm$^2$ protein adsorption. Because of the high hydration and ultralow fouling properties of zwitterionic materials, zwitterionic hydrogels are of interest as hydrogels with superior suitability for biomedical applications. The zwitterionic hydrogels studied so far, however, have shown low mechanical strength, which limits their potential biological uses.

A need therefore exists for hydrogels having improved mechanical properties. The present invention seeks to fulfill this need and provides further related advantages.

SUMMARY OF THE INVENTION

The present invention provides functionalized zwitterionic and mixed charge polymers and copolymers, methods for making the polymers and copolymers, hydrogels prepared from the functionalized zwitterionic and mixed charge polymers and copolymers, methods for making the hydrogels, methods for using the hydrogels for in vitro and in vivo cell culture, and zwitterionic and mixed charge polymers and copolymers for administration for therapeutic agents.

Functionalized Zwitterionic Polymers and Mixed Charge Copolymers

In one aspect, the invention provides functionalized zwitterionic polymers and copolymers and functionalized mixed charge copolymers.

In one embodiment, the invention provides a functionalized polymer, comprising a core having two or more polymeric branches covalently coupled to and extending from the core, wherein the polymeric branches comprises constitutional units selected from the group consisting of zwitterionic constitutional units and mixed charge constitutional units, and wherein the two or more polymeric branches each comprise one or more functional groups effective for covalently coupling the polymer to a material capable of forming a covalent bond with the one or more functionalize groups.

In certain embodiments, the polymer comprises three, four, five, or six polymeric branches. The number of branches can be varied and depends in the nature of the core and the branches themselves. In some embodiments, the branches are branched.

In certain embodiments, the constitutional units are zwitterionic constitutional units. In other embodiments, the constitutional units are mixed charge constitutional units. It will be appreciated that the zwitterionic polymers and mixed charge copolymers may further include other constitutional units (e.g., the zwitterionic polymers can be copolymers). Suitable other constitutional units include constitutional units that include functional groups for imparting reactivity to the copolymers, or other groups to impart desired properties to the copolymer (e.g., anionic groups, cationic groups, neutral groups, hydrophobic groups, hydrophilic groups).

In certain embodiments, the functional group is positioned at the terminus of the polymeric branch. In other embodiments, the functional group is positioned along the backbone of the polymeric branch. In some embodiments, one or more of the constitutional units comprise the functional group. The number of functional groups in the polymer or the polymer branch can be controlled to achieve the desired overall functionality of the polymer or branch and will depend on the polymers ultimate use.

In certain embodiments, the functional group is a thiol. In other embodiments, the functional group is one of a reactive pair. In these embodiments, the functional group is one of a reactive pair selected from an azide and an alkyne, an azide and an alkene, a thiol and a maleimide, or a thiol and a dissulfide.

Zwitterionic and Mixed Charge Polymeric Hydrogels

In another aspect of the invention, zwitterionic and mixed charge hydrogels are provided.

In one embodiment, the hydrogel comprises a first polymer covalently coupled to a second polymer, wherein the first polymer comprises a first core having two or more polymeric branches covalently coupled to and extending from the first core, wherein the polymeric branches comprise first constitutional units selected from the group consisting of zwitterionic constitutional units and mixed charge constitutional units, and wherein the two or more polymeric branches each comprise one or more first functional groups effective for covalently coupling the first polymer to the second polymer, wherein the second polymer comprises a second core having two or more polymeric branches covalently coupled to and extending from the second core, wherein the polymeric branches comprise second constitutional units selected from the group consisting of zwitterionic constitutional units and mixed charge constitutional units, and wherein the two or more polymeric branches each comprise one or more second functional groups effective for covalently coupling the second polymer to the first polymer; and wherein the hydrogel comprises covalent bonds linking the first and second polymers formed by reaction of the first and second functional groups.

In another embodiment, the hydrogel comprises a first polymer covalently coupled to a second polymer, wherein the first polymer comprises a first core having two or more polymeric branches covalently coupled to and extending from the first core, wherein the polymeric branches comprise first constitutional units selected from the group consisting of zwitterionic constitutional units and mixed charge constitutional units, and wherein the two or more polymeric branches each comprise one or more first functional groups effective for covalently coupling the first polymer to the second polymer, wherein the second polymer comprises a second core having two or more polymeric branches covalently coupled to and extending from the second core, wherein the polymeric branches comprise second constitutional units selected from the group consisting of zwitterionic constitutional units and mixed charge constitutional units, and wherein the two or more polymeric branches each comprise one or more second functional groups effective for covalently coupling the second polymer to the first polymer; and wherein the hydrogel comprises covalent bonds linking the first and second polymers via a crosslinking agent having two or more third functional groups, wherein the covalent bonds linking the first and second polymers are formed by reaction of the first and third functional groups and the second and third functional groups.

In certain of the hydrogel embodiments that include crosslinks formed by a crosslinking agent, it will be appreciated that the nature of crosslinking can be varied. In certain embodiments, the first and second polymers are different, have different functional groups, and are crosslinked by the crosslinking agent with suitably reactive functional groups. In other embodiments, the first and second polymers are the same, have the same functional groups, and are crosslinked by the crosslinking agent with suitably reactive functional groups.

In certain of the hydrogel embodiments that include crosslinks formed by a crosslinking agent, the first and second functional groups are the same. In certain of the hydrogel embodiments that include crosslinks formed by a crosslinking agent, the first functional group is a thiol, the second functional group is a thiol, and the third functional group is a thiol or a disulfide. In other of the hydrogel embodiments that include crosslinks formed by a crosslinking agent, the first and third functional groups and the second and third functional groups are click chemistry reactive pairs. In certain of these embodiments, the first and third functional groups are selected from an azide and an alkyne, an azide and an alkene, a thiol and a maleimide, or a thiol and a disulfide. In certain of these embodiments, the second and third functional groups are selected from an azide and an alkyne, an azide and an alkene, a thiol and a maleimide, or a thiol and a disulfide.

For the hydrogels of the invention as described above, in certain embodiments, the first polymer comprises three, four, five, or six polymeric branches. In certain embodiments, the first constitutional units are zwitterionic constitutional units. In other embodiments, the first constitutional units are mixed charge constitutional units.

In certain embodiments, the first functional groups are positioned at the terminus of the polymeric branch. In other embodiments, the first functional groups are positioned along the backbone of the polymeric branch. In certain embodiments, the first constitutional units comprise the first functional group.

In certain embodiments, the second polymer comprises three, four, five, or six polymeric branches. In certain embodiments, the second constitutional units are zwitterionic constitutional units. In other embodiments, the second constitutional units are mixed charge constitutional units.

In certain embodiments, the second functional groups are positioned at the terminus of the polymeric branch. In other embodiments, the second functional groups are positioned along the backbone of the polymeric branch. In certain embodiments, the second constitutional units comprise the second functional group.

In certain embodiments, the first and second functional groups are the same. In certain embodiments, the first functional group is a thiol and second functional group is a thiol. In other embodiments, the first and second functional groups are different. In certain embodiments, the first and second functional groups are a click chemistry reactive pair. Representative pairs include an azide and an alkyne, an azide and an alkene, a thiol and a maleimide, or a thiol and a dissulfide.

The hydrogel of the invention may advantageously include additional components. In certain embodiment, the hydrogels further include cells, viruses, bacteria, and components thereof, or their genetically altered variants.

Representative cells include natural cells and their genetically modified counterparts, such as exocrine secretory epithelial cells, hormone secreting cells, keratinizing epithelial cells, wet stratified barrier epithelial cells, sensory transducer cells, autonomic neuron cells, sense organ and peripheral neuron supporting cells, neurons and glial cells, lens cells, hepatocytes, adipocytes, lipocytes, barrier function cells, kidney cells, heart cells, extracellular matrix cells, contractile cells, blood and immune system cells such as erythrocytes, monocytes, neutrophils, mast cells, T cells, stem cells, germ cells, nurse cells, interstitial cells, progenitor cells, hematopoietic stem cells.

Representative viruses include DNA viruses, RNA viruses, reverse transcriptase viruses, retroviruses, and adenoviruses.

Representative bacteria include pathogenic bacteria, Gram-positive bacteria, Gram-negative bacteria, cyanobacteria. Representative bacteria species include clostridial species, *S. typhimurium*, and *E. coli*.

In certain embodiments, the hydrogels of the invention include oligonucleotides (DNAs and RNAs), lipoplexes, polymersomes, polyplexes, dendrimers, inorganic particles.

In other embodiments, the hydrogels of the invention include proteins, peptides, polysaccharides, or small molecules.

In certain embodiments, the hydrogels of the invention include a therapeutic or diagnostic agent.

In other embodiments, the hydrogels of the invention include a nanomaterial.

Surfaces Treated and Devices Made with Zwitterionic and Mixed Charge Polymeric Hydrogels In a further aspect, the invention provides substrates treated a hydrogel of the invention. In one embodiment, the invention provides a substrate having a surface, wherein at least a portion of the surface is coated with the hydrogel. In certain embodiments, the surface is entirely coated with the hydrogel.

In a related aspect, the invention provides devices (e.g., medical devices) formed at least in part from the hydrogels of the invention or devices (e.g., medical devices) that incorporate the hydrogels of the invention. In certain of these embodiments, the devices are made entirely or partially from the hydrogels of the invention.

Representative substrates and devices include the following: implantable biosensor, wound care device, sealant, contact lens, dental implant, orthopedic device (artificial joint, artificial bone, artificial ligament, artificial tendon), cardiovascular device (cathether, artificial valve, artificial vessel, artificial stent, LVAD, rhythm management device), gastroenterology device (feeding tube, alimentary canal clip, gastro-intestinal sleeve, gastric balloon), OB/Gyn device (implantable birth control device, vaginal sling), nephrology device (anastomotic connector, subdermal port), neurosurgery device (nerve guidance tube, cerebrospinal fluid drain or shunt), dermatology device (skin repair device), ophthalmic device (shunt), otorhinolaryngology device (stent, cochlear implant, tube, shunt, spreader), intra-ocular lens. aesthetic implant (breast implant, nasal implant, cheek implant), neurologic implant (nerve stimulation device), cochlear implant, nerve conduit, hormone control implant (blood sugar sensor, insulin pump), implanted biosensor, access port device, tissue scaffold pulmonic device (valve for management of COPD or artificial lungs), radiology device (radio-opaque or sono-opaque markers), or urology device (catheter, artificial urethrae).

Zwitterionic and Mixed Charge Polymeric Hydrogels Uses

In another aspect, the invention provides uses for the zwitterionic and mixed charge polymeric hydrogels.

In certain embodiments, the invention provides a medium for protection, preservation, or growth of cells comprising the hydrogel. The medium can further include one or more nutrients or growth factors. The medium can be used in vitro or in vivo.

In certain embodiments, the invention provides a surgical sealant comprising the hydrogel.

In certain embodiments, the invention provides a surgical anti-adherence coating comprising the hydrogel.

In certain embodiments, the invention provides a surgical filler comprising the hydrogel.

In certain embodiments, the invention provides a wound dressing comprising the hydrogel.

In certain embodiments, the invention provides an aesthetic filler comprising the hydrogel.

In certain embodiments, the invention provides an aesthetic filler pre-formed to a specific shape comprising the hydrogel.

In certain embodiments, the invention provides an orthopedic soft tissue replacement (e.g., for cartilage or spinal discs) comprising the hydrogel.

In certain embodiments, the invention provides a tissue growth scaffold, comprising the hydrogel. The scaffold can be used in vitro or in vivo.

In certain embodiments, the invention provides a medical device formed at least in part from a hydrogel.

In certain embodiments, the invention provides a medical device incorporating a hydrogel.

Methods for Making Zwitterionic and Mixed Charge Polymeric Hydrogels

In a further aspect, the invention provides methods for making zwitterionic and mixed charge polymeric hydrogels.

In a first embodiment, the invention provides a method for forming a hydrogel, comprising reacting a first polymer with a second polymer to provide a hydrogel, wherein the first polymer comprises a first core having two or more polymeric branches covalently coupled to and extending from the first core, wherein the polymeric branches comprise first constitutional units selected from the group consisting of zwitterionic constitutional units and mixed charge constitutional units, and wherein the two or more polymeric branches each comprise one or more first functional groups effective for covalently coupling the first polymer to the second polymer, wherein the second polymer comprises a second core having two or more polymeric branches covalently coupled to and extending from the second core, wherein the polymeric branches comprise second constitutional units selected from the group consisting of zwitterionic constitutional units and mixed charge constitutional units, and wherein the two or more polymeric branches each comprise one or more second functional groups effective for covalently coupling the second polymer to the first polymer; and wherein the hydrogel is formed by covalent bond formation between the first and second functional groups.

In certain embodiments, the hydrogel is formed in situ (e.g., in vivo). In other embodiments, the hydrogel is formed in a vessel. In either embodiment, the hydrogel can be used for cell culture.

In a second embodiment, the invention provides a method for forming a hydrogel in vivo, comprising:

(a) disposing a first polymer at a site in vivo; and (b) disposing a second polymer at the site, whereby the second polymer contacts the first polymer at the site to provide a hydrogel, wherein the first polymer comprises a first core having two or more polymeric branches covalently coupled to and extending from the first core, wherein the polymeric branches comprise first constitutional units selected from the group consisting of zwitterionic constitutional units and mixed charge constitutional units, and wherein the two or more polymeric branches each comprise one or more first functional groups effective for covalently coupling the first polymer to the second polymer, wherein the second polymer comprises a second core having two or more polymeric branches covalently coupled to and extending from the second core, wherein the polymeric branches comprise second constitutional units selected from the group consisting of zwitterionic constitutional units and mixed charge constitutional units, and wherein the two or more polymeric branches each comprise one or more second functional groups effective for covalently coupling the second polymer to the first polymer; and wherein the hydrogel is formed by covalent bond formation between the first and second functional groups.

In certain embodiments, the first polymer and second polymer are disposed at the site by injection, spray, pouring, and dipping.

In a third embodiment, the invention provides a method for forming a hydrogel, comprising reacting a first polymer, a second polymer, and a crosslinking agent to provide a hydrogel, wherein the first polymer comprises a first core having two or more polymeric branches covalently coupled to and extending from the first core, wherein the polymeric branches comprise first constitutional units selected from the group consisting of zwitterionic constitutional units and mixed charge constitutional units, and wherein the two or more polymeric branches each comprise one or more first functional groups effective for covalently coupling the first polymer to the crosslinking agent, wherein the second polymer comprises a second core having two or more polymeric branches covalently coupled to and extending from the second core, wherein the polymeric branches comprise second constitutional units selected from the group consisting of zwitterionic constitutional units and mixed charge constitutional units, and wherein the two or more polymeric branches each comprise one or more second functional groups effective for covalently coupling the second polymer to the crosslinking agent; wherein the crosslinking agent comprises two or more third functional groups effective for covalently coupling the first polymer to the second polymer by forming crosslinks between the first and second polymers; and wherein the hydrogel is formed by covalent bond formation between the first and third functional groups and the second and third functional groups.

In certain embodiments of the third embodiment, the first and second functional groups are the same; the first functional group is a thiol, the second functional group is a thiol, and the third functional group is a thiol or a disulfide; and the first and third functional groups and the second and third functional groups are click chemistry reactive pairs. In certain embodiments, the first and third functional groups are selected from an azide and an alkyne, an azide and an alkene, a thiol and a maleimide, or a thiol and a dissulfide. In certain embodiments, the second and third functional groups are selected from an azide and an alkyne, an azide and an alkene, a thiol and a maleimide, or a thiol and a dissulfide.

In the above methods (first, second, and/or third embodiments), the first polymer comprises three, four, five, or six polymeric branches.

In certain of these embodiments, the first constitutional units are zwitterionic constitutional units. In others of these embodiments, the first constitutional units are mixed charge constitutional units.

In certain embodiments, the first functional groups are positioned at the terminus of the polymeric branch. In other embodiments, the first functional groups are positioned along the backbone of the polymeric branch. In certain embodiments, one or more of the first constitutional units comprise the first functional group.

In the above methods (first, second, and/or third embodiments), the second polymer comprises three, four, five, or six polymeric branches.

In certain of these embodiments, the second constitutional units are zwitterionic constitutional units. In others of these embodiments, the second constitutional units are mixed charge constitutional units.

In certain embodiments, the second functional groups are positioned at the terminus of the polymeric branch. In other embodiments, the second functional groups are positioned along the backbone of the polymeric branch. In certain embodiments, one or more of the second constitutional units comprise the second functional group.

In certain embodiments, the first and second functional groups are the same. In certain embodiments, the first functional group is a thiol and second functional group is a thiol.

In other embodiments, the first and second functional groups are different. In certain embodiments, the first and second functional groups are a click chemistry reactive pair. In certain embodiments, the first and second functional groups are selected from an azide and an alkyne, an azide and an alkene, a thiol and a maleimide, or a thiol and a dissulfide.

Zwitterionic and Mixed Charge Star Polymer Therapeutic Agent Conjugates

In another aspect, the invention provides zwitterionic and mixed charge star polymer therapeutic agent conjugates.

In one embodiment, the invention provides a polymer, comprising a core having two or more polymeric branches covalently coupled to and extending from the core, wherein the polymeric branches comprises constitutional units selected from the group consisting of zwitterionic constitutional units and mixed charge constitutional units, and wherein the zwitterionic constitutional units and the mixed charge constitutional units comprise a therapeutic agent covalently coupled thereto.

In certain embodiments, the therapeutic agent is covalently coupled to the constitutional unit by a hydrolyzable bond.

In certain embodiments, the polymer comprises three, four, five, or six polymeric branches. In certain embodiments, the constitutional units are zwitterionic constitutional units. In other embodiments, the constitutional units are mixed charge constitutional units.

In a related aspect, a method for administering a therapeutic agent to a subject is provided. In the method, a therapeutically effective amount of a polymer of the invention having a therapeutic agent covalently coupled thereto is administered to a subject (e.g., a warm-blooded animal, such as a human) in need thereof.

In certain embodiments, administering the polymer comprises systemic, topical, or local administration. In certain embodiments, administering the polymer comprises inhalation, oral, and transdermal administration. In certain embodiments, administering the polymer comprises intravenous injection, intramuscular injection, subcutaneous injection, intraperitoneal injection, or local injection.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 3A illustrates the syntheses of two representative star polymers of the invention: (a) a star polymer having zwitterionic (polycarboxybetaine) branches terminated with a thiol group ($-CH_2-SH$) denoted pCB-A; and (b) a star polymer having zwitterionic (polycarboxybetaine) branches terminated with a pyridyl disulfide group (—CH$_2$—S—S—C$_5$H$_4$N) denoted pCB-B. These star polymers were prepared from the star polymer illustrated in FIG. 1 by click chemistry (reaction of the star polymer with sodium azide and (a) 3-thioacetylene or (b) 3-pyridyl disulfide acetylene). FIG. 3B illustrates the preparation of representative hydrogels of the invention prepared from reaction of the star polymers (pCB-A and pCB-B) illustrated in FIG. 3A. The hydrogels can be formed by simply mixing pCB-A with pCB-B in the presence of cells.

FIG. 4A is an image showing the results of a LIVE/DEAD assay performed on encapsulated islets within pCB hydrogels after 18-day in vitro culture. Scale bar: 300 µm. Effects of hydrogel encapsulation of islet cells is shown in FIGS. 4B-4D. FIG. 4B compares glucose consumption over time for islet cells cultured in a representative hydrogel of the invention (pCB) and control (Ctrl) (n=3). FIG. 4C compares insulin secretion in static incubation on day 18 (n=4) for islet cells cultured in a representative hydrogel of the invention (pCB) and control (Ctrl). FIG. 4D compares dynamic insulin release on day 18 for islet cells cultured in a representative hydrogel of the invention (pCB) and control (Ctrl) as assessed by sequential stimulating by low (3 mM, blue arrow), high (17 mM, red arrow), and low (3 mM) glucose media again using a perifusion system (n=3). In the figures, * indicates significant difference from control islets (without hydrogel, p<0.05). Mean±SEM.

FIG. 5A illustrates hydrogel modulus over time (hydrogel degradation). FIG. 5B is an image showing the results of a LIVE/DEAD assay performed on encapsulated PBSC cells within the pCB hydrogels after 7-day in vitro culture.

As shown in FIG. 6, the therapeutic agent is ibuprophen, and the monomer for synthesizing the star polymer capable of releasing ibuprophen is prepared by condensation of CBMA with ibuprofen.

DETAILED DESCRIPTION OF THE INVENTION

Figure 1:
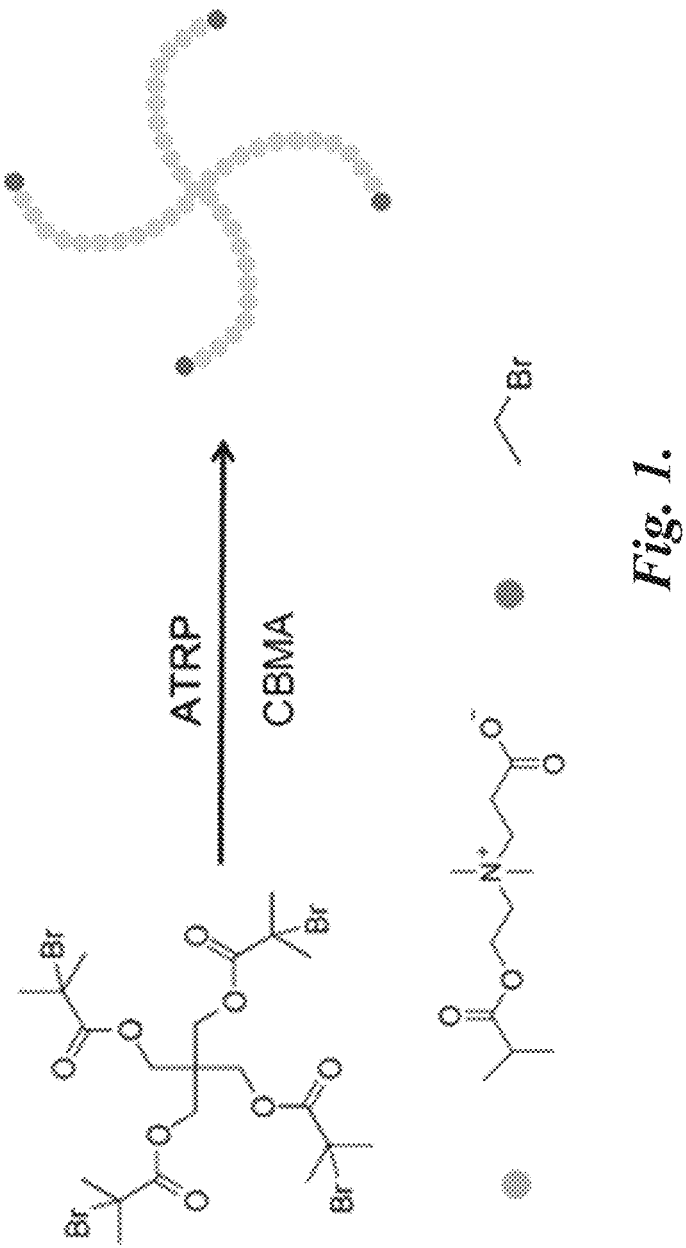
FIG. 1 is a schematic illustration of the synthesis of a representative star polymer of the invention having zwitterionic (polycarboxybetaine) branches. In this star polymer the branches are shown terminating with a bromomethyl group, which is the radical initiator group for continued polymerization (e.g., atom transfer radical polymerization, ATRP). The star polymer was prepared by ATRP from the tetrafunctional core having the illustrated radical initiator groups ($-O(C=O)-C(CH_3)_2-Br$) and carboxybetaine methacrylate ($CH_2=C(CH_3)-C(=O)-CH_2CH_2-N(CH_3)_2^+-CH_2CH_2-CO_2^-$, CBMA) monomers.

The present invention provides zwitterionic and mixed charge star polymers and copolymers, functionalized zwitterionic and mixed charge star polymers and copolymers useful for therapeutic agent delivery and hydrogel formations, zwitterionic and mixed charge star polymers and copolymers having therapeutic agents covalently coupled thereto for therapeutic agent delivery, and hydrogels prepared from the functionalized zwitterionic and mixed charge star polymers.

As used herein, the term "zwitterionic polymer or copolymer" refers to a polymer or copolymer having zwitterionic constitutional units. Zwitterionic constitutional units have pendant groups (i.e., groups pendant from the polymer backbone) that include zwitterionic groups. Representative zwitterionic pendant groups include carboxybetaine groups (e.g., —R$_a$—N$^+$(R$_b$)(R$_c$)—R$_d$—CO$_2$$^-$, where R$_a$ is a linker group that covalently couples the polymer backbone to the cationic nitrogen center of the carboxybetaine groups, R$_b$ and R$_c$ are nitrogen substituents, R$_d$ is a linker group that covalently couples the cationic nitrogen center to the carboxy group of the carboxybetaine group).

The term "mixed charge copolymer" refers to a copolymer having substantially equal numbers of positively charged constitutional units and negatively charged constitutional units to provide a copolymer that is substantially electronically neutral. In certain embodiments, the mixed charge copolymer are random copolymers that do not have extensive regions along the polymer backbone that are positively charged or negatively charged (i.e., the positively and negatively charged constitutional units are relatively uniformly distributed along the polymer backbone). Representative mixed charge pendant groups include carboxy groups (e.g., —R$_a$—CO$_2$$^-$, where R$_a$ is a linker group that covalently couples the carboxy group to the polymer backbone) and amino groups (e.g., —R$_a$—N$^+$(R$_b$)(R$_c$)(R$_d$), where R$_a$ is a linker group that covalently couples the cationic nitrogen center to the polymer backbone, and R$_b$, R, and R$_d$ are nitrogen substituents).

The term "star polymer or copolymer" refers to a branched polymer or copolymer in which two or more polymer or copolymer branches extend from a core. Representative star polymers and copolymers of the invention include two, three, four, five, six, or more branches extending from the core. The core is a group of atoms having two or more functional groups from which the branches can be extended by polymerization. Representative cores have two, three, four, five, six, or more functional groups from which the branches can be extended. In certain embodiments, the branches are zwitterionic polymeric or copolymeric branches. In other embodiments, the branches are mixed charge copolymeric branches The term "functionalized polymer or copolymer" refers to a polymer of copolymer that includes a functional group that renders to polymer or copolymer reactive to covalent coupling to another polymer of copolymer that is also a functionalized polymer or copolymer. In the practice of the invention, functionalized star polymers and copolymers of the invention react through their functional groups to form covalent bonds that covalently couple the polymers and copolymers (e.g., crosslink the polymer and copolymers). To covalently couple a first functionalized polymer or copolymer to a second functionalized polymer or copolymer, the functional groups of the first and second polymers or copolymers (i.e., the first and second functional groups, respectively) have complimentary reactivity. The first and second functional groups are reactive pairs. In certain embodiments, the first and second functional groups react on mixing at a temperature between room temperature and physiological temperature to form a bond (e.g., without external stimulus). Suitable such reactive pairs are known in the art. Representative useful reactive pairs include thiol/maleimide and click chemistry reactive pairs (e.g., azides/alkynes and azides/alkenes).

Polymer Definitions

The term "constitutional unit" refers to an atom or group of atoms in a polymer that includes a part of the polymer chain together with its pendant atoms or groups of atoms, if any. The constitutional unit can refer to a repeat unit. The constitutional unit can also refer to an end group on a polymer chain. For example, the constitutional unit of polyethylene glycol can be —$CH_2CH_2O$— corresponding to a repeat unit, or —$CH_2CH_2OH$ corresponding to an end group.

The term "repeat unit" corresponds to the smallest constitutional unit, the repetition of which constitutes a regular macromolecule (or oligomer molecule or block).

The term "end group" refers to a constitutional unit with only one attachment to a polymer chain, located at the end of a polymer. For example, the end group can be derived from a monomer unit at the end of the polymer, once the monomer unit has been polymerized. As another example, the end group can be a part of a chain transfer agent or initiating agent that was used to synthesize the polymer.

The term "monomer" is a polymerizable compound that, on polymerization, contributes one or more constitutional units in the structure of the polymer.

The term "polymer" refers to the product that is the result of polymerization of a single monomer.

The term "copolymer" refers to a polymer that is the result of polymerization of two or more different monomers. The number and the nature of each constitutional unit can be separately controlled in a copolymer. The constitutional units can be disposed in a purely random, an alternating random, a regular alternating, a regular block, or a random block configuration unless expressly stated to be otherwise. A purely random configuration can, for example, be: x-x-y-z-x-y-y-z-y-z-z-z . . . or y-z-x-y-z-y-z-x-x . . . . An alternating random configuration can be: x-y-x-z-y-x-y-z-y-x-z . . . , and a regular alternating configuration can be: x-y-z-x-y-z-x-y-z . . . .

Functionalized Zwitterionic Polymers and Mixed Charge Copolymers

In one aspect, the invention provides functionalized zwitterionic and mixed charge polymers and copolymers. In certain embodiments, the functionalized zwitterionic and mixed charge polymers and copolymers of the invention are functionalized zwitterionic star and mixed charge star polymers and copolymers.

As noted above, for the star polymers and copolymers of the invention, the branches can be any zwitterionic or mixed charge polymers and their precursors that can be converted to zwitterionic or mixed charge polymers via hydrolysis, ultraviolet irradiation, or heat. The zwitterionic or mixed charge polymers can be obtained by any polymerization method effective for polymerization of unsaturated monomers, including atom transfer radical polymerization (ATRP), reversible addition-fragmentation chain-transfer polymerization (RAFT), photo-polymerization, ring-opening polymerization (ROP), condensation, Michael addition, branch generation/propagation reaction, or other reactions. In certain embodiments, the polymers having terminal functional groups are able to specifically bind to a binding partner and at the same time avoid nonspecific biofouling, which is imparted to the polymers by their zwitterionic or mixed charge structures. By virtue of their functionalized terminal ends, the polymers of the invention can be converted to further functionalized polymers useful for making hydrogels of the invention, by complimentary coupling chemistries (e.g., click chemistries, thiol exchange reactions, reductive reactions, and other chemistries known in the art). These functional end groups can be pre- and post-modified after the branches are created.

Zwitterionic Monomers.

In certain embodiments, the functionalized polymers, and copolymers of the invention are polymers prepared from polymerization of suitable polymerizable zwitterionic monomers. In certain of these embodiments, the polymer or copolymer has repeating units having formula (I):

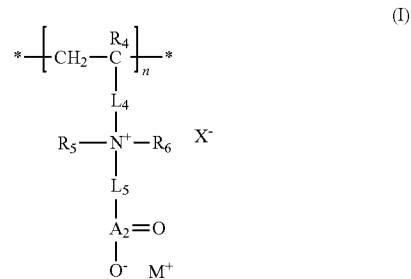

wherein $R_4$ is selected from hydrogen, fluorine, trifluoromethyl, C1-C6 alkyl, and C6-C12 aryl groups;

$R_5$ and $R_6$ are independently selected from alkyl and aryl, or taken together with the nitrogen to which they are attached form a cationic center;

$L_4$ is a linker that covalently couples the cationic center [$N^+(R_5)(R_6)$] to the polymer backbone [—($CH_2$—$CR_4$)$_n$—];

$L_5$ is a linker that covalently couples the anionic center [$A_2(=O)O^-$] to cationic center;

$A_2$ is C, SO, $SO_2$, P, or PO;

n is an integer from 5 to about 10,000; and

* represents the point at which the repeating unit is covalently linked to an adjacent repeating unit or a functional group useful for forming hydrogels.

In the polymer, the pendant zwitterionic groups are internal salts and $M^+$ and $X^-$ are absent.

In one embodiment, $R_4$ is C1-C3 alkyl.

$R_5$ and $R_6$ are independently selected from alkyl and aryl, or taken together with the nitrogen to which they are attached form a cationic center. In one embodiment, $R_5$ and $R_6$ are C1-C3 alkyl.

In certain embodiments, $L_4$ is selected from the group consisting of —C(=O)O—(CH$_2$)$_n$— and —C(=O)NH—(CH$_2$)$_n$—, wherein n is an integer from 1 to 20. In certain embodiments, $L_4$ is —C(=O)O—(CH$_2$)$_n$—, wherein n is 1-6.

In certain embodiments, $L_5$ is —(CH$_2$)$_n$—, where n is an integer from 1 to 20.

In certain embodiments, $A_2$ is C or SO.

In certain embodiments, n is an integer from 5 to about 5,000.

In one embodiment, $R_4$, $R_5$, and $R_6$ are methyl, $L_4$ is —C(=O)O—(CH$_2$)$_2$—, $L_5$ is —(CH$_2$)—, $A_1$ is C, and n is an integer from 10 to about 1,000.

The zwitterionic polymers and copolymers of the invention can be prepared by polymerization of monomers having formula (II):

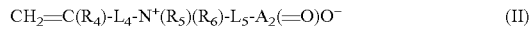

CH$_2$=C(R$_4$)-L$_4$-N$^+$(R$_5$)(R$_6$)-L$_5$-A$_2$(=O)O$^-$    (II)

wherein $R_4$, $R_5$, $R_6$, $L_4$, $L_5$, and $A_2$, are as described above for the repeating unit of formula (I).

Representative zwitterionic polymer branches of the invention have formula (III):

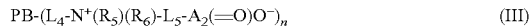

PB-(L$_4$-N$^+$(R$_5$)(R$_6$)-L$_5$-A$_2$(=O)O$^-$)$_n$    (III)

wherein $R_5$, $R_6$, $L_4$, $L_5$, $A_2$, and n are as described above for the repeating unit of formula (I), and PB is the polymer backbone that includes repeating units [formula (I)].

Mixed Charge Comonomers.

In another aspect, the invention provides mixed charge copolymers prepared from copolymerization of ion pair comonomers. As noted above, the mixed charge copolymers having a polymer backbone, a plurality of positively charged repeating units, and a plurality of negatively charged repeating units. In the practice of the invention, these copolymers may be prepared by polymerization of ion-pair comonomers.

The mixed charge copolymer includes a plurality of positively charged repeating units, and a plurality of negatively charged repeating units. In one embodiment, the mixed charge copolymer is substantially electronically neutral. As used herein, the term "substantially electronically neutral" refers to a copolymer that imparts advantageous nonfouling properties to the copolymer. In one embodiment, a substantially electronically neutral copolymer is a copolymer having a net charge of substantially zero (i.e., a copolymer about the same number of positively charged repeating units and negatively charged repeating units). In one embodiment, the ratio of the number of positively charged repeating units to the number of the negatively charged repeating units is from about 1:1.1 to about 1:0.5. In one embodiment, the ratio of the number of positively charged repeating units to the number of the negatively charged repeating units is from about 1:1.1 to about 1:0.7. In one embodiment, the ratio of the number of positively charged repeating units to the number of the negatively charged repeating units is from about 1:1.1 to about 1:0.9.

In one embodiment, the mixed charge copolymers are prepared from copolymerization of suitable polymerizable ion pair comonomers.

Representative ion-pair comonomers useful in the invention have formulas (IV) and (V):

CH$_2$=C(R$_7$)-L$_6$-N$^+$(R$_9$)(R$_{10}$)(R$_{11}$)X$^-$    (IV)

CH$_2$=C(R$_8$)-L$_7$-A$_3$(=O)—O$^-$-M$^+$    (V)

In this embodiment, the mixed charge copolymer has repeating units having formula (VI):

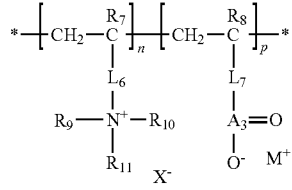

(VI)

wherein $R_7$ and $R_8$ are independently selected from hydrogen, fluorine, trifluoromethyl, C1-C6 alkyl, and C6-C12 aryl groups;

$R_9$, $R_{10}$, and $R_{11}$ are independently selected from alkyl and aryl, or taken together with the nitrogen to which they are attached form a cationic center;

$A_3$(=O)OM) is an anionic center, wherein $A_3$ is C, SO, SO$_2$, P, or PO, and M is a metal or organic counterion;

$L_6$ is a linker that covalently couples the cationic center [N$^+$(R$_9$)(R$_{10}$)(R$_{11}$)] to the polymer backbone;

$L_7$ is a linker that covalently couples the anionic center [A(=O)OM] to the polymer backbone;

X$^-$ is the counter ion associated with the cationic center;

n is an integer from 5 to about 10,000;

p is an integer from 5 to about 10,000; and

* represents the point at which the repeating units is covalently linked to either and adjacent repeating unit or a functional group useful for forming hydrogels.

In one embodiment, $R_7$ and $R_8$ are C1-C3 alkyl.

$R_9$, $R_{10}$, and $R_{11}$ are independently selected from alkyl and aryl, or taken together with the nitrogen to which they are attached form a cationic center. In one embodiment, $R_9$, $R_{10}$, and $R_{11}$ are C1-C3 alkyl.

In certain embodiments, $L_6$ is selected from the group consisting of —C(=O)O—(CH$_2$)$_n$— and —C(=O)NH—(CH$_2$)$_n$—, wherein n is an integer from 1 to 20. In certain embodiments, $L_6$ is —C(=O)O—(CH$_2$)$_n$—, wherein n is 1-6.

In certain embodiments, $L_7$ is a C1-C20 alkylene chain. Representative $L_7$ groups include —(CH$_2$)—, where n is 1-20 (e.g., 1, 3, or 5)

In certain embodiments, $A_3$ is C, S, SO, P, or PO.

In certain embodiments, n is an integer from 5 to about 5,000.

In one embodiment, $R_7$, $R_8$, $R_9$, $R_{10}$, and $R_{11}$ are methyl, $L_6$ and $L_7$ are —C(=O)O—(CH$_2$)$_2$—, $A_1$ is C, and n is an integer from 10 to about 1,000.

Representative mixed charge copolymer branches have formula (VII):

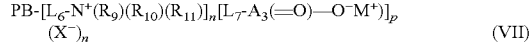

PB-[L$_6$-N$^+$(R$_9$)(R$_{10}$)(R$_{11}$)]$_n$[L$_7$-A$_3$(=O)—O$^-$M$^+$)]$_p$
(X$^-$)$_n$    (VII)

wherein $L_6$, N$^+$(R$_9$)(R$_{10}$)(R$_{11}$), L$_7$, A$_3$(=O)O-M$^+$, X$^-$, n, and p are as described above, and PB is the polymer backbone that includes repeating units [formula (VI)].

The following is a description of the crosslinking agent, monomers, comonomers, polymers, copolymers, and cross-links of formulas (I)-(VI) described above.

In the above formulas, PB is the polymer backbone. Representative polymer backbones include vinyl backbones (e.g., —C(R')(R")—C(R''')(R'''')—, where R', R", R''', and R'''' are independently selected from hydrogen, alkyl, and aryl) derived from vinyl monomers (e.g., acrylate, methacrylate, acrylamide, methacrylamide, styrene). Other suitable backbones include polymer backbones that provide for pendant groups. Other representative polymer backbones include peptide (polypeptide), urethane (polyurethane), and epoxy backbones.

Similarly, in the above formulas, $CH_2=C(R)$— is the polymerizable group. It will be appreciated that other polymerizable groups, including those noted above, can be used to provide the monomers and polymers of the invention.

In the above formulas, $N^+$ is the cationic center. In certain embodiments, the cationic center is a quaternary ammonium (e.g., N bonded to $L_4$, $R_5$, $R_6$, and $L_5$). In addition to ammonium, other useful cationic centers ($R_5$ and $R_6$ taken together with N) include imidazolium, triazaolium, pyridinium, morpholinium, oxazolidinium, pyrazinium, pyridazinium, pyrimidinium, piperazinium, and pyrrolidinium.

$R_4$, $R_5$, $R_6$, $R_9$, $R_{10}$, and $R_{11}$ are independently selected from hydrogen, alkyl, and aryl groups. Representative alkyl groups include C1-C10 straight chain and branched alkyl groups. In certain embodiments, the alkyl group is further substituted with one of more substituents including, for example, an aryl group (e.g., —$CH_2C_6H_5$, benzyl). Representative aryl groups include C6-C12 aryl groups including, for example, phenyl. For certain embodiments of the above formulas, $R_5$ and $R_6$, or $R_9$, $R_{10}$, and $R_{11}$ are taken together with $N^+$ form the cationic center.

$L_4$ (or $L_6$) is a linker that covalently couples the cationic center to the polymer backbone. In certain embodiments, $L_4$ includes a functional group (e.g., ester or amide) that couples the remainder of $L_4$ to the polymer backbone (or polymerizable moiety for the monomers). In addition to the functional group, $L_4$ can include a C1-C20 alkylene chain. Representative $L_4$ groups include —C(=O)O—$(CH_2)_n$— and —C(=O)NH—$(CH_2)_n$—, where n is 1-20 (e.g., 3).

$L_5$ is a linker that covalently couples the cationic center to the anionic group (i.e., (A=O)O$^-$). $L_5$ can be a C1-C20 alkylene chain. Representative $L_5$ groups include —$(CH_2)_n$—, where n is 1-20 (e.g., 1, 3, or 5).

$L_7$ is a linker that covalently couples the polymer backbone to the anionic group. $L_7$ can be a C1-C20 alkylene chain. Representative $L_7$ groups include —$(CH_2)_n$—, where n is 1-20 (e.g., 1, 3, or 5).

A(=O)—O$^-$ is the anionic center. The anionic center can be a carboxylic acid ester (A is C), a sulfinic acid (A is SO), a sulfonic acid (A is $SO_2$), a phosphinic acid (A is P), or a phosphonic acid (A is PO).

In the above formulas, representative alkyl groups include C1-C30 straight chain and branched alkyl groups. In certain embodiments, the alkyl group is further substituted with one of more substituents including, for example, an aryl group (e.g., —$CH_2C_6H_5$, benzyl).

Representative aryl groups include C6-C12 aryl groups including, for example, phenyl including substituted phenyl groups (e.g., benzoic acid).

$X^-$ is the counter ion associated with the cationic center. The counter ion can be the counter ion that results from the synthesis of the cationic polymers or the monomers (e.g., Cl$^-$, Br$^-$, I$^-$). The counter ion that is initially produced from the synthesis of the cationic center can also be exchanged with other suitable counter ions to provide polymers having controllable hydrolysis properties and other biological properties. Representative hydrophobic counter ions include carboxylates, such as benzoic acid and fatty acid anions (e.g., $CH_3(CH_2)_nCO_2^-$ where n=1-19); alkyl sulfonates (e.g., $CH_3(CH_2)_nSO_3^-$ where n=1-19); salicylate; lactate; bis(trifluoromethylsulfonyl)amide anion ($N^-(SO_2CF_3)_2$); and derivatives thereof. Other counter ions also can be chosen from chloride, bromide, iodide, sulfate; nitrate; perchlorate ($ClO_4$); tetrafluoroborate ($BF_4$); hexafluorophosphate ($PF_6$); trifluoromethylsulfonate ($SO_3CF_3$); and derivatives thereof. Other suitable counter ions include hydrophobic counter ions and counter ions having therapeutic activity (e.g., an antimicrobial agent, such as salicylic acid (2-hydroxybenzoic acid), benzoate, lactate.

For the monomers, $R_1$ and $R_2$ is selected from hydrogen, fluoride, trifluoromethyl, and C1-C6 alkyl (e.g., methyl, ethyl, propyl, butyl). In one embodiment, $R_1$, $R_2$, and $R_4$ are hydrogen. In one embodiment, $R_1$, $R_2$, and $R_4$ are methyl.

Figure 2:
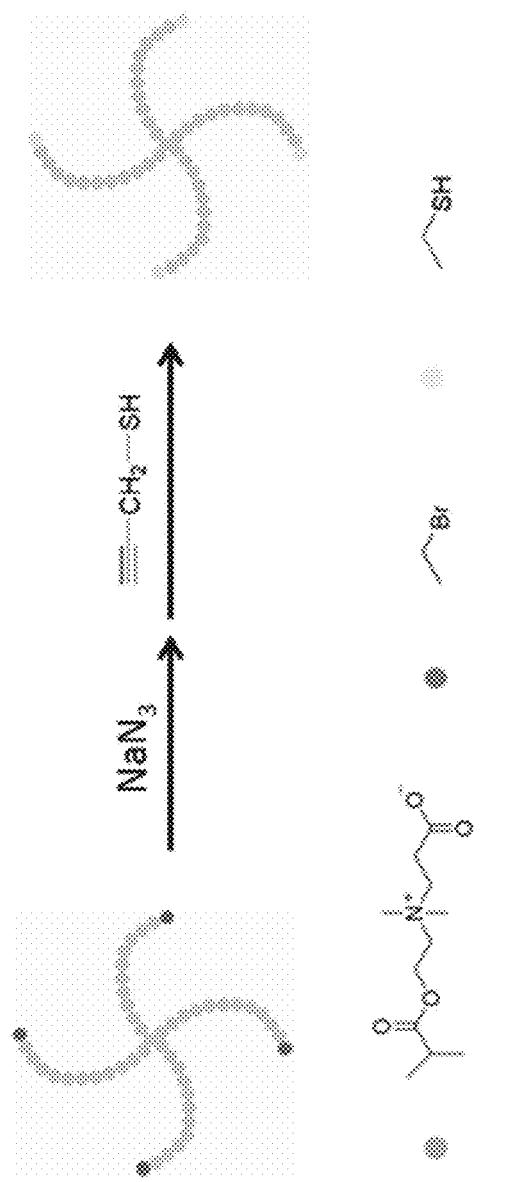
FIG. 2 is a schematic illustration of the synthesis of a representative star polymer of the invention having zwitterionic (polycarboxybetaine) branches terminated with a thiol group ($-CH_2-SH$). This star polymer was prepared from the star polymer illustrated in FIG. 1 by click chemistry (reaction of the star polymer with sodium azide and 3-thioacetylene).

Representative zwitterionic star polymers of the invention are illustrated in FIGS. 1 and 2.

FIG. 1 is a schematic illustration of the synthesis of a representative star polymer of the invention having zwitterionic (polycarboxybetaine) branches. In this star polymer the branches are shown terminating with a bromomethyl group, which is the radical initiator group for continued polymerization (e.g., atom transfer radical polymerization, ATRP). The star polymer was prepared by ATRP from the tetrafunctional core having the illustrated radical initiator groups (—O(C=O)—$C(CH_3)_2$—Br) and carboxybetaine methacrylate ($CH_2=C(CH_3)$—C(=O)—$CH_2CH_2$—N$(CH_3)_2^+$—$CH_2CH_2$—$CO_2^-$, CBMA) monomers.

FIG. 2 is a schematic illustration of the synthesis of a representative star polymer of the invention having zwitterionic (polycarboxybetaine) branches terminated with a thiol group (—$CH_2$—SH). This star polymer was prepared from the star polymer illustrated in FIG. 1 by click chemistry (reaction of the star polymer with sodium azide and 3-thioacetylene).

Representative functional groups for the zwitterionic and mixed charge polymers of the invention include OH, NH, $NH_2$, SH, $N_3$, CH=$CH_2$, C≡CH, COOH, CHO, imidoester, haloacetyl, hydrazide, alkoxyamine, aryl azide, diazirine, maleimide, carbodiimide, N-hydroxysuccinimide (NHS), thiazolidine-2-thione, pyridyldisulfide, difluorinatedcyclooctyne, Staudinger reagent pairs, isocyanate, isothiocyanate, thioether, sulfhydryl, hydrazine, hydroxymethyl phosphine, sulfo-NHS ester, pentafluorophenyl ester, sulfonylazide, 5H-dibenz[b,f]azepine, and their derivatives.

In certain embodiments, the functionalized zwitterionic polymer has formula (A):

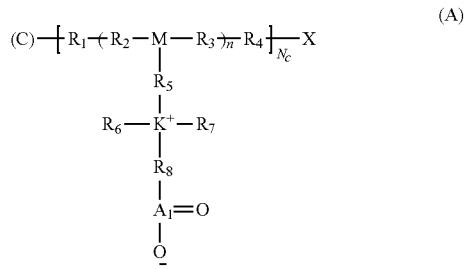

(A)

wherein (C) is a core (e.g., C1-C50 alkylene, arylene, acrylate, amine, amide, or other macromolecular cores);

$R_1$, $R_4$, $R_5$, $R_8$, and M are independently selected from the group consisting of C—C6 alkylene and C6-C12 arylene.

$R_2$ and $R_3$ are independently selected from the group consisting of C1-C6 alkylene, C6-C12 arylene, —O$(CH_2)_m$—, —S$(CH_2)_m$—, —C(=O)$(CH_2)_m$—, —C(=S)$(CH_2)_m$—, —C(=NH)$(CH_2)_m$— and —NH$(CH_2)_m$—, —$(CH_2)_mC(=O)$—, —$(CH_2)_mOC(=O)$—, —$(CH_2)_m$NHC (=O)—, —(CH$_2$)$_m$NHC(=S)—, —(CH$_2$)$_m$SC(=O)—, —(CH$_2$)$_m$SC(=S)—, —(CH$_2$)$_m$NHC(=NH)—, and —(CH$_2$)$_m$C(=O)NHNH—, wherein m is an integer from 1 to 20;

K is a cationic center selected from the group consisting of ammonium, imidazolium, triazolium, pyridinium, morpholinium, and other nitrogen-, sulfide-, phosphate-based cations, such as ammoniophosphinates, ammonio(alkoxy)dicyanoethenolates, ammonioboronates, sulfoniocarboxylates, and oxypyridinebetaines;

$R_6$ and $R_7$ are independently selected from the group consisting of hydrogen and C1-C6 alkyl, or taken together with K form a cationic center selected from the group consisting of ammonium, imidazolium, triazolium, pyridinium, morpholinium, and other nitrogen-, sulfide-, phosphate-based cations, such as ammoniophosphinates, ammonio(alkoxy)dicyanoethenolates, ammonioboronates, sulfoniocarboxylates, and oxypyridinebetaines;

$A_1$ is C, SO, SO$_2$, P, or PO$^-$;

n is an integer from 5 to about 10,000;

$N_c$ is core multiplicity and is an integer from 1 to 1000; and

X is a functional group selected from the group consisting of OH, NH, NH$_2$, SH, N$_3$, CH=CH$_2$, C≡CH, COOH, CHO, imidoester, haloacetyl, hydrazide, alkoxyamine, aryl azide, diazirine, maleimide, carbodiimide, N-hydroxysuccinimide (NHS), thiazolidine-2-thione, pyridyldisulfide, difluorinatedcyclooctyne, one of a Staudinger reagent pair, isocyanate, isothiocyanate, thioether, sulfhydryl, hydrazine, hydroxymethyl phosphine, sulfo-NHS ester, pentafluorophenyl ester, sulfonylazide, 5H-dibenz[b,f]azepine, and their derivatives.

Core multiplicity ($N_c$) is the total number of branches in the polymer. In certain embodiments, the number of branches is from 2 to 500, 3 to 100, 3 to 10, 3 to 6.

In certain embodiments, X is a thiol, a disulfide, a maleimide, or one of a click chemistry reactive pair.

In other embodiments, the functionalized zwitterionic polymer has formula (B):

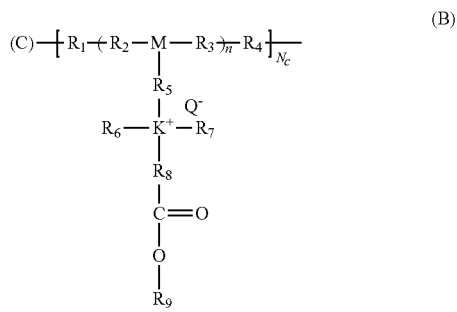

wherein (C), $R_1$, $R_2$, $R_3$, $R_4$, $R_5$, $R_6$, $R_7$, $R_8$, M, K, n, and $N_c$, are as described above for (A);

$Q^-$ is a counter ion selected from Cl$^-$, Br$^-$, I$^-$, SO$_4^{2-}$, NO$_3^-$, ClO$_4^-$, BF$_4^-$, PF$_6^-$, N(SO$_2$CF$_3$)$_2^-$, SO$_3$CF$_3^-$, or RCOO$^-$ (where R is a C1-C20 alkyl group), or lactate, benzoate, salicylate, and derivatives; and $R_9$ is a functional group selected from the group consisting of hydrogen, trifluoromethyl, C1-C6 alkyl, C6-C12 aryl, —(CH$_2$)$_n$OH, —(CH$_2$)$_n$NH$_2$, —(CH$_2$)$_n$SH, —(CH$_2$)$_n$N$_3$, —(CH$_2$)$_n$CH=CH$_2$, —(CH$_2$)$_n$C≡CH, —(CH$_2$)$_n$COOH, —(CH$_2$)$_n$CHO, where n is 1 to 6, imidoester, haloacetyl, hydrazide, alkoxyamine, aryl azide, diazirine, maleimide, carbodiimide, N-hydroxysuccinimide (NHS), thiazolidine-2-thione, pyridyldisulfide, difluorinatedcyclooctyne, one of a Staudinger reagent pair, isocyanate, isothiocyanate, thioether, sulfhydryl, hydrazine, hydroxymethyl phosphine, sulfo-NHS ester, pentafluorophenyl ester, sulfonylazide, 5H-dibenz[b,f]azepine, and their derivatives.

In further embodiments, the functionalized zwitterionic polymer has formula (C):

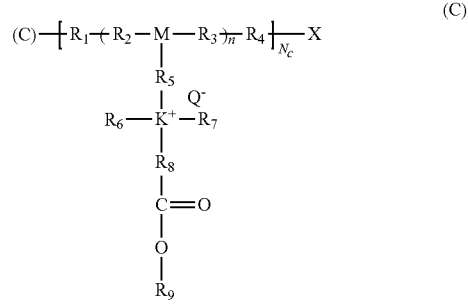

wherein (C), $R_1$, $R_2$, $R_3$, $R_4$, $R_5$, $R_6$, $R_7$, $R_8$, $R_9$, M, K, Q, X, n, and $N_c$, are as described above for (A) and (B).

In other embodiments, the functionalized zwitterionic polymer has formula (D):

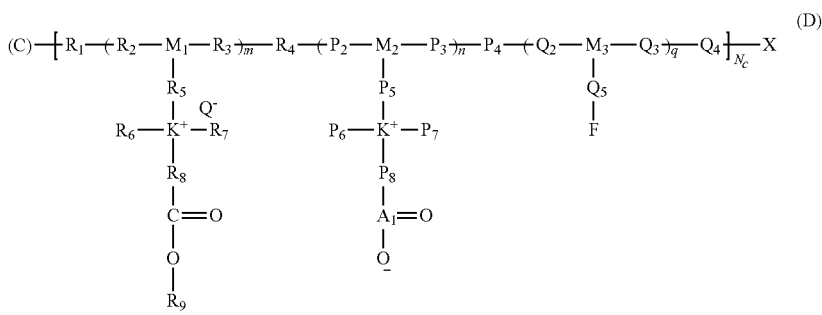

wherein $R_1$, $R_2$, $R_3$, $R_4$, $R_5$, $R_6$, $R_7$, $R_8$, Q, $A_1$, $N_c$, and X are as described above for (A), (B), and (C), $M_1$, $M_2$, and $M_3$ are independently selected and are as described above for M for (A), (B), and (C);

$K_1$ and $K_2$ are independently selected and are as described above for K for (A), (B), and (C);

$P_2$ and $P_3$ are as described above for $R_2$ and $R_3$;

$P_4$, $P_5$, and $P_8$ are as described above for $R_4$, $R_5$, and $R_8$, respectively;

$P_6$ and $P_7$ are as described above for $R_6$ and $R_7$;

$Q_2$ and $Q_3$ as described above for $R_2$ and $R_3$;

$Q_4$ and $Q_5$ are as described above for $R_4$ and $R_5$;

$R_9$, F, and X are functional groups independently selected from the group consisting of $-(CH_2)_nOH$, $-(CH_2)_nNH_2$, $-(CH_2)_nSH$, $-(CH_2)_nN_3$, $-(CH_2)_nCH=CH_2$, $-(CH_2)_nC\equiv CH$, $-(CH_2)_nCOOH$, $-(CH_2)_nCHO$, where n is 1 to 6, imidoester, haloacetyl, hydrazide, alkoxyamine, aryl azide, diazirine, maleimide, carbodiimide, N-hydroxysuccinimide (NHS), thiazolidine-2-thione, pyridyldisulfide, difluorinatedcyclooctyne, one of a Staudinger reagent pair, isocyanate, isothiocyanate, thioether, sulfhydryl, hydrazine, hydroxymethyl phosphine, sulfo-NHS ester, pentafluorophenyl ester, sulfonylazide, 5H-dibenz[b,f]azepine, and their derivatives.

m is an integer from 5 to about 10,000;

n is an integer from 5 to about 10,000; and q is an integer from 5 to about 10,000.

In certain embodiments, the functionalized mixed charge copolymer has formula (E):

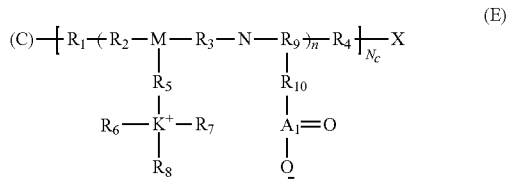

(E)

wherein (C), $R_1$, $R_2$, $R_3$, $R_5$, $R_6$, $R_7$, M, K, $A_1$, n, $N_c$, and X are as described above for (A), and N is as described above for M;

$R_8$ is as described above for $R_6$ and $R_7$.

$R_9$ is as described above for $R_2$ and $R_3$.

$R_{10}$ is as described above for $R_5$.

In other embodiments, the functionalized mixed charge copolymer has formula (F):

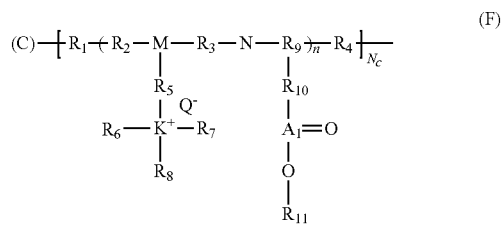

(F)

wherein (C), $R_1$, $R_2$, $R_3$, $R_4$, $R_5$, $R_6$, $R_7$, $R_8$, $R_9$, $R_{10}$, M, K, N, $A_1$, n, and $N_c$, are as described above for (E), $Q^-$ is as described above for (B), and $R_{11}$ is selected from the group consisting of $-(CH_2)_nOH$, $-(CH_2)_nNH_2$, $-(CH_2)_nSH$, $-(CH_2)_nN_3$, $-(CH_2)_nCH=CH_2$, $-(CH_2)_nC\equiv CH$, $-(CH_2)_nCOOH$, $-(CH_2)_nCHO$, where n is 1 to 6, imidoester, haloacetyl, hydrazide, alkoxyamine, aryl azide, diazirine, maleimide, carbodiimide, N-hydroxysuccinimide (NHS), thiazolidine-2-thione, pyridyldisulfide, difluorinatedcyclooctyne, one of a Staudinger reagent pair, isocyanate, isothiocyanate, thioether, sulfhydryl, hydrazine, hydroxymethyl phosphine, sulfo-NHS ester, pentafluorophenyl ester, sulfonylazide, 5H-dibenz[b,f]azepine, and their derivatives.

In further embodiments, the functionalized mixed charge copolymer has formula (G):

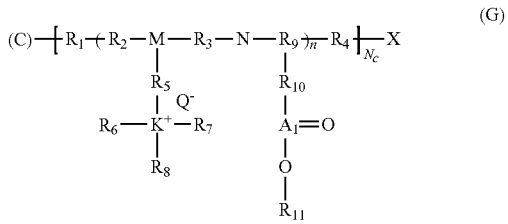

(G)

wherein (C), $R_1$, $R_2$, $R_3$, $R_4$, $R_5$, $R_6$, $R_7$, $R_8$, $R_9$, $R_{10}$, $R_{11}$, M, K, N, $A_1$, n, $N_c$, and X are as described above for (E) and (F).

In other embodiments, the functionalized mixed charge copolymer has formula (H):

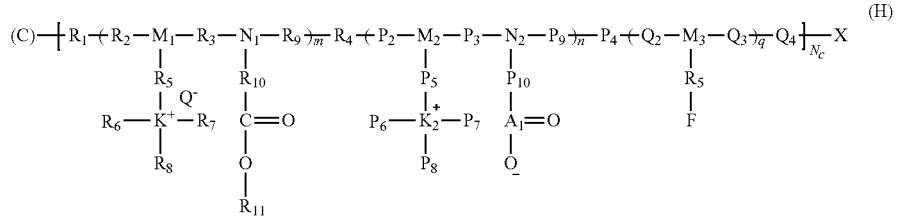

(H)

wherein (C), $R_1$, $R_2$, $R_3$, $R_4$, $R_5$, $R_6$, $R_7$, $R_8$, $R_9$, $R_{10}$, $R_{11}$, $A_1$, $N_c$, $Q^-$, and X are as described above for (G);

$M_1$, $M_2$, and $M_3$ are independently M as described above for (G);

$N_1$ and $N_2$ are independently N as described above for (G);

$K_1$ and $K_2$ are independently K as described above for (G);

$P_2$, $P_3$, and $P_9$ are as for $R_2$, $R_3$, and $R_9$, respectively;

$P_4$ is as for $R_4$;

$P_5$ and $P_{10}$ are as for $R_5$ and $R_{10}$, respectively;

$P_6$, $P_7$, and $P_8$ are as for $R_6$, $R_7$, and $R_8$, respectively;

$Q_2$, $Q_3$, and $Q_4$ are as for $R_2$, $R_3$, and $R_4$, respectively;

F is as described above for (D); and m, n, and q are as described above for (D).

Zwitterionic and Mixed Charge Polymeric Hydrogels

In a further aspect, the invention provides hydrogels prepared from the functionalized zwitterionic and mixed charge star polymers. Functionalized zwitterionic and mixed charge polymers and copolymers can be used to form homopolymers or copolymers (e.g., hydrogels) by use of the same polymer (e.g., via disulfide linkage of thiol terminated polymers), two or more polymers (e.g. via click chemistry), or with other multifunctional molecules, oligomers, and polymers.

Figure 10:
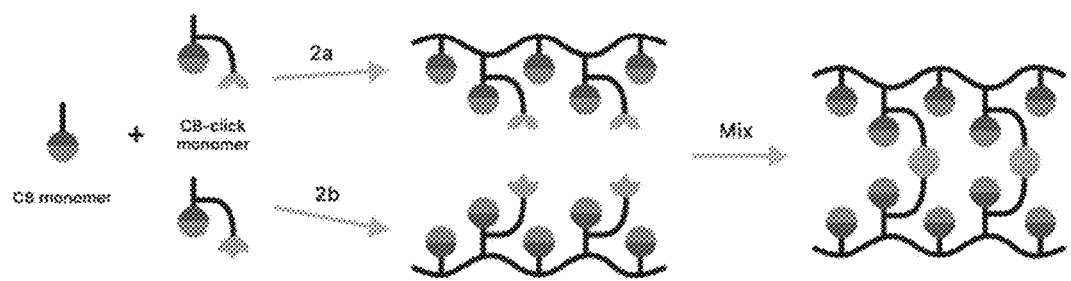
FIG. 10 depicts poly(carboxybetaine) copolymers functionalized with complimentary clickable groups R and R* (steps 2a and 2b) by copolymerization and the resulting hydrogel formed by their mixing.
Figure 11:
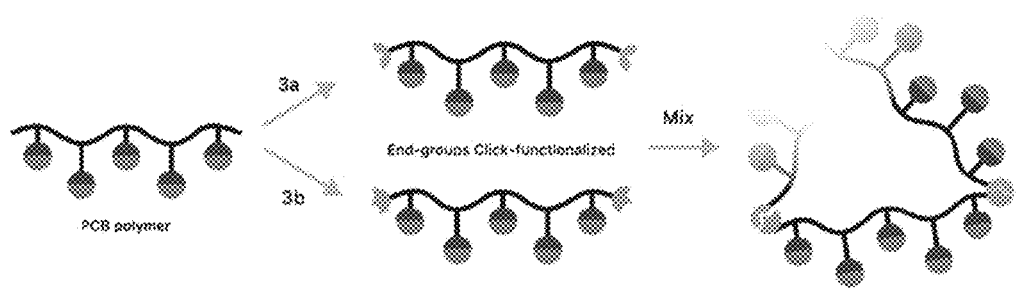
FIG. 11 depicts end-group functionalized polymers and hydrogel formed from the polymers.

Poly(carboxybetaine) (pCB) polymers are highly functionalizable due to the presence of abundant carboxylic acid (COOH) groups in the polymer (i.e., present in each constitutional unit). Such functionality renders the polymer versatile for further functionalized with simple chemistries. One such chemistry is the coupling of the COOH group with amine functional compounds. This chemistry is simple to carry out due to the high efficiency of coupling agents (e.g., N-(3-dimethylaminopropyl)-N'-ethylcarbodiimide hydrochloride/N-hydroxysuccinimide (EDC/NHS)). Coupling chemistry can be used to functionalize pCB polymers with a variety of different amines. When amines are selected that contain complimentary groups for click chemistry, pairs of click-reactive pCB polymers can be obtained. Hydrogel of the invention can be prepared by simply mixing the two polymers with complimentary functional groups. In other embodiments, a suitable bifunctional crosslinker or other complimentary functionalized compound can be mixed with a reactive pCB polymer to provide a hydrogel. These concepts are illustrated in FIGS. 9-11.

In one embodiment, first and second zwitterionic polymers (e.g., pCBs) functionalized with complimentary clickable groups (R and R*) are combined to provide a hydrogel as shown in Scheme 1.

Figure 9:
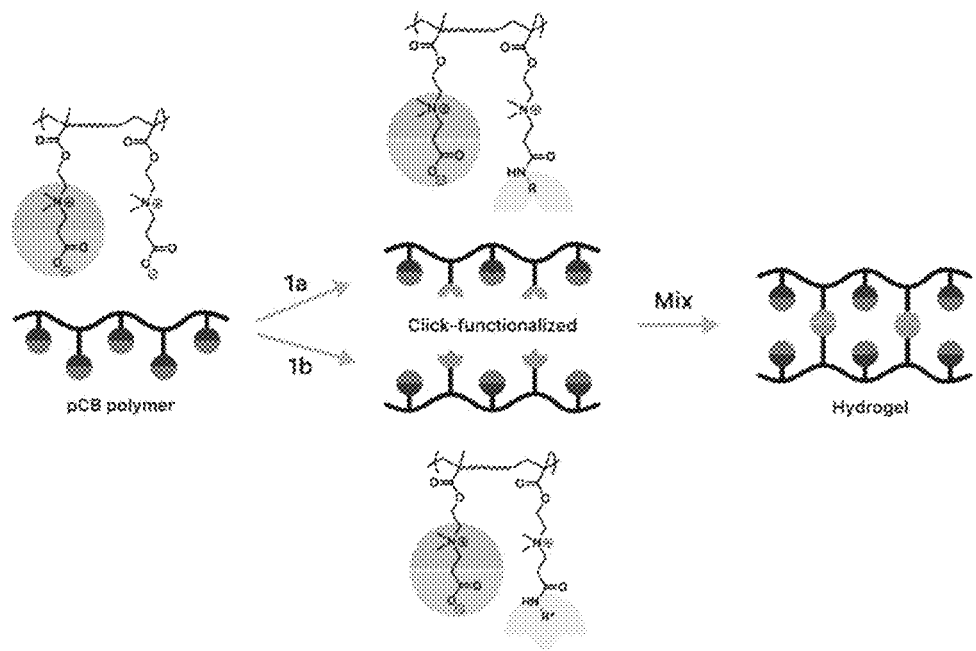
FIG. 9 shows poly(carboxybetaine) polymers functionalized with complimentary clickable groups R and R* (steps 1a and 1b) and the resulting hydrogel formed by their mixing.

Referring to FIG. 9, a first polymer bearing pendant first reactive groups (R) and a second polymer bearing pendant second reactive groups (R*) are combined to provide a representative hydrogel of the invention. The first and second polymers can be prepared from the same polymer as shown in FIG. 9 (e.g., a zwitterionic polymer or mixed charge copolymer of the invention). The hydrogel is formed by crosslinking the first and second polymers through the complimentary first and second reactive groups (e.g., complimentary first and second click groups)

In another embodiment, first and second complimentary reactive (e.g., click-reactive) polymers can be prepared by copolymerization of zwitterionic monomer (e.g., CBMA) and first and second comonomers, respectively. The first comonomer includes a first reactive group (e.g., a zwitterionic monomer that further includes the first reactive group, such as a click-reactive group). The second comonomer includes a second reactive group (e.g., a zwitterionic monomer that further includes the second reactive group, such as a click-reactive group). This copolymerization strategy may be used where a high degree of functionalization is required, such as for preparing a high-strength injectable hydrogel to mimic cartilage or other tissue. By these methods, functionality and overall zwitterionic character of the polymer is maintained. This strategy is shown in FIG. 10.

Referring to FIG. 10 path 2a, a first zwitterionic copolymer is prepared by copolymerization of a zwitterionic monomer (denoted CB monomer) (e.g., CBMA) and a first comonomer (denoted CB-click monomer) that includes a first reactive group (i.e., a zwitterionic comonomer that further includes the first reactive (e.g., first click-reactive) group). Referring to FIG. 10 path 2b, a second zwitterionic copolymer is prepared by copolymerization of a zwitterionic monomer (denoted CB monomer) (e.g., CBMA) and a second comonomer (denoted CB-click monomer) that includes a second reactive group (e.g., a zwitterionic monomer that further includes the second reactive (e.g., second click-reactive) group, as shown in 2a. The hydrogel is formed by crosslinking the first and second polymers through the complimentary first and second reactive groups (e.g., complimentary first and second click reactive groups).

In a further embodiment, zwitterionic polymers may be end-group functionalized with complimentary reactive (e.g., click-reactive) groups. See FIG. 11. These end-group functionalized polymers can be used with the polymers and copolymers illustrated in FIGS. 9 and 10. The preparation of end-group functionalized polymers and the hydrogel formed by their mixing is shown in FIG. 11.

Referring to FIG. 11 path 3a, a first zwitterionic polymer is end-group functionalized with a first reactive group (e.g., first click-reactive group). Referring to FIG. 11 path 3b, a second zwitterionic polymer is end-group functionalized with a second reactive group (e.g., second click-reactive group). The hydrogel is formed by crosslinking the first and second polymers through the complimentary first and second reactive groups (e.g., complimentary first and second click reactive groups).

The crosslinking (hydrogel-forming) chemistries above are described as reaction between complimentary reactive groups (i.e., first and second reactive groups). It will be appreciated that the complimentary reactive groups can be any pair of reactive groups having reactivity suitable for bond formation, preferably reactivity suitable for bond formation at temperatures between room and physiological temperature. In certain embodiments, the complimentary reactive groups are click groups (click-reactive pairs), which are well known in the art.

Representative zwitterionic click hydrogels formed using the strategies described above are set forth in Examples 1-6.

The hydrogels can take the form of a scaffold, an injectable hydrogel or nanogel with or without biotic compounds. In certain embodiments, the hydrogels of the present invention further comprise encapsulated small molecules, nanomaterials, nucleic acids, polysaccharides, proteins, and cells. Such hydrogels have applications in medical and pharmaceutical sensing, orthopedics, cardiovascular, internal ophthalmic, aesthetic, ocular and drug/protein/drug delivery. The hydrogels can be attached to surfaces for medical and engineering applications. In addition to forming hydrogels, functionalized zwitterionic polymers can also be attached to biotic or non-biotic molecules and substrates. Furthermore, for functionalizable polycarboxybetaine (PCB) polymers, the polymer can be conjugated directly in a degradable or non-degradable way while branches can be replaced by as acrylamide, oxazoline, and vinylpyrrolidone.

The hydrogels of the invention can be used for objects, devices, and components, such as implantable biosensors; wound care devices, glues and sealants, a contact lens; a dental implant; an orthopedic device such as an artificial joint, an artificial bone, an artificial ligaments, and an artificial tendon; a cardiovascular device such as a cathether, an artificial valve, an artificial vessel, an artificial stent, LVADs, or a rhythm management device; gastroenterology devices such as feeding tubes, alimentary canal clips, gastrointestinal sleeves, or gastric balloons; OB/Gyn devices such as implantable birth control devices or vaginal slings; nephrology devices such as anastomotic connectors or subdermal ports; neurosurgery devices such as nerve guidance tubes, cerebrospinal fluid drains or shunts, dermatology devices such as skin repair devices an ophthalmic device such as a shunt, otorhinolaryngology devices such as stents, cochlear implants, tubes, shunts or spreaders, an intra-ocular lense; an aesthetic implant such as a breast implant, a nasal implant, and a cheek implant; a neurologic implant such as a nerve stimulation device, a cochlear implant, and a nerve conduit; a hormone control implant such as a blood sugar sensor and an insulin pump; an implanted biosensor; an access port device; and a tissue scaffold pulmonic devices such as valves for management of COPD or artificial lungs; radiology devices such as radio-opaque or sono-opaque markers; or urology devices such as catheters or artificial urethrae.

The following is a description of representative hydrogels of the invention and their use for cell culture and tissue scaffolds.

Functionalized Zwitterionic Polymers-Based Hydrogel for Islets Encapsulation.

Functionalized star-shaped poly(carboxybetaine) polymers (pCB) prepared by polymerization of CBMA were synthesized via a combination of ATRP and click chemistry. Thiol group-terminated pCB polymers was synthesized, and pCB hydrogels were formed by mixing thiol-terminated pCBs with 1,2-bis(maleimido)ethane together under physiological conditions.

The synthesis of star pCB polymer via ATRP was conducted as illustrated in FIG. 1. Briefly, CBMA, 2,2'-bipyridine (bpy), catalysts, and tetrafunctional initiator, pentaerythritoltetrakis(2-bromoisobutyrate) were placed in a 10 mL reaction tube, and the mixture was subjected to three freeze-pump-thaw cycles. The mixture was held at room temperature for 20 min, and water and methanol were added at a 1:1 ratio. The reaction was allowed to continue at room temperature under stirring for 8 h. The polymer product was recovered after treatment with alumina, and finally purified by precipitation twice into acetone. The molecular weight of the polymer can be tuned by the stoichiometric ratio between the monomer and the initiator. Star polymers with molecular weights of 5000, 20,000 and 50,000 were synthesized. Other living polymerization methods, such as RAFT. can also be applied to synthesize the polymer. The functionalized star pCB polymers were prepared by click chemistry. As shown in FIG. 2, after purification, the terminal bromine groups of the initially formed star pCB were transformed into azido groups by a nucleophilic substitution reaction with sodium azide in water. The product was purified by dialysis. Lyophilization was used to remove the water. pCB-$N_3$ (pCB-azide) chains were then reacted with the alkyne-SH in methanol with CuBr/PMDETA as catalyst to produce the star pCB polymers with four arm. As illustrated in FIG. 2, thiol-terminated star pCB was obtained after purification via dialysis and lyophilization.

Figure 3A:
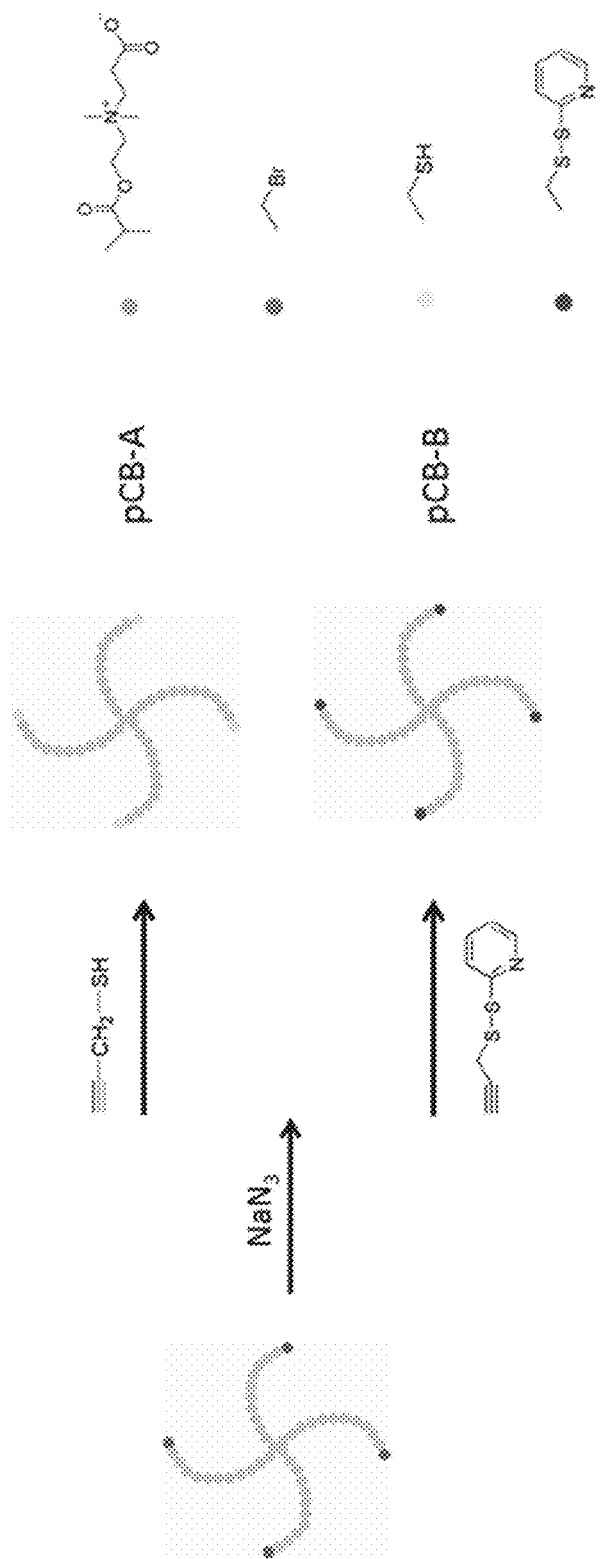
FIGS. 3A and 3B schematically illustrate the preparation of a representative hydrogel of the invention prepared from suitably functionalized star polymers of the invention.
Figure 3B:
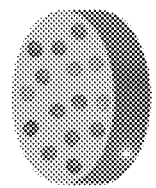
Figure 3B:
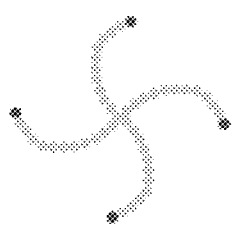
Figure 3B:
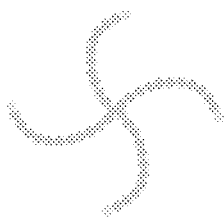

FIGS. 3A and 3B schematically illustrate the preparation of a representative hydrogel of the invention prepared from suitably functionalized star polymers of the invention. FIG. 3A illustrates the syntheses of two representative star polymers of the invention: (a) a star polymer having zwitterionic (polycarboxybetaine) branches terminated with a thiol group ($-CH_2-SH$) denoted pCB-A; and (b) a star polymer having zwitterionic (polycarboxybetaine) branches terminated with a pyridyl disulfide group ($-CH_2-S-S-C_5H_4N$) denoted pCB-B. These star polymers were prepared from the star polymer illustrated in FIG. 1 by click chemistry (reaction of the star polymer with sodium azide and (a) 3-thioacetylene or (b) 3-pyridyl disulfide acetylene). FIG. 3B illustrates the preparation of representative hydrogels of the invention prepared from reaction of the star polymers (pCB-A and pCB-B) illustrated in FIG. 3A. The hydrogels can be formed by simply mixing pCB-A with pCB-B in the presence of cells.

Figure 4A:
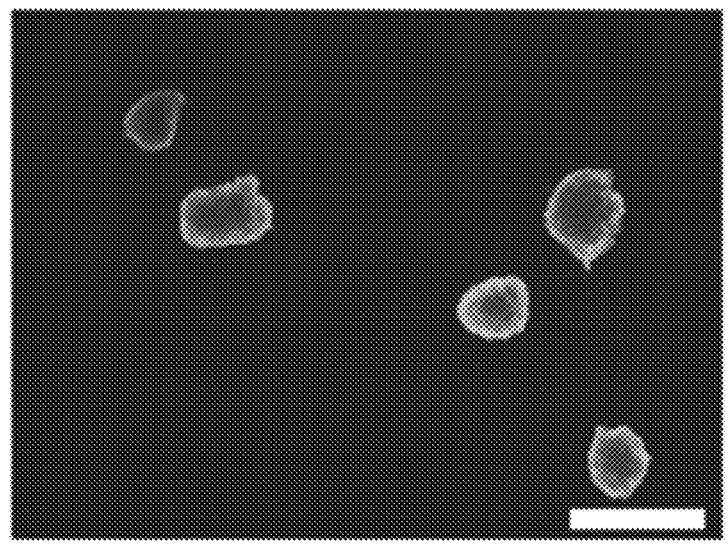
FIGS. 4A-4D present data for encapsulated islets cells cultured in a representative hydrogel (pCB hydrogel) of the invention.
Figure 4B:
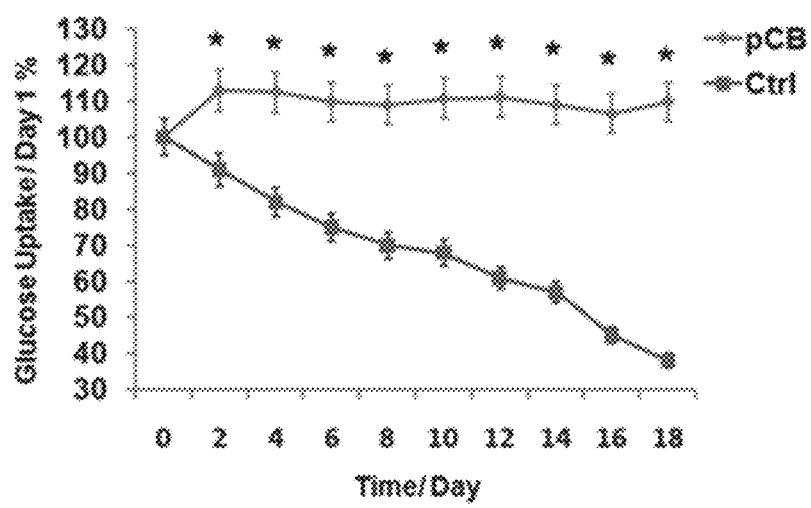
Figure 4C:
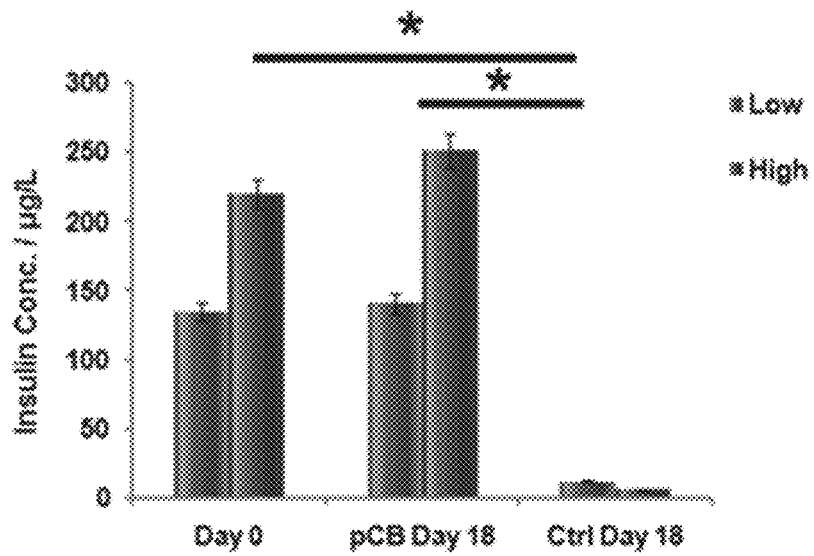
Figure 4D:
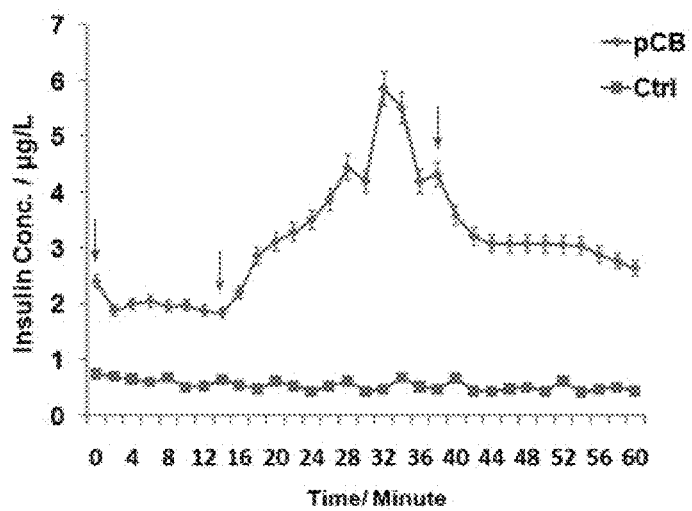

In vitro islet encapsulation and analysis in pCB hydrogel was evaluated. Rat islets were mixed with 5% thiol-terminated pCB-A (MW=15000) in RPMI-1640 medium. Then, 1,2-bis(maleimido)ethane was added to the mixture and the system was allowed to cure at 37° C. for 5 min. Hydrogel-encapsulated islets and control islets were cultured with RPMI-1640 culture medium, supplemented with 10% FBS at 37° C., with media changed every two days. As shown in FIG. 4A, encapsulated islets exhibited very high viability after the 18-day culture in vitro. Glucose consumption in culture media was used to measure the metabolic activity of hydrogel-encapsulated islets maintained in culture. Glucose metabolism was measured primarily by the glucose utilization in medium by the cultured islets and shown as an indicator not only for islet viability, but also cellular activity. The uptake of glucose in medium was measured every 48 h over the 18 day period to assess islet quality. Glucose uptake in encapsulated islets was maintained near 100% of the day 1 level until day 18 (FIG. 4B). In control islets, glucose consumption decreased to 72% by day 7, and further declined as time progressed. By day 14 and 18, only 59% and 38% of the glucose was utilized, respectively. Overall, encapsulated islets maintained much higher metabolic activity as compared to control islets (p<0.01). To quantify the biosynthetic capacity of insulin, cultured islets were incubated in either low (3 mM) or high (17 mM) glucose medium for 18 h on day 0 and day 18 (FIG. 4B). Hydrogel-encapsulated islets maintained insulin secretion levels of freshly isolated islets (day 0) in both high- and low-glucose exposure (p=0.13-0.40). In contrast, the glucose responsiveness was not preserved in the control cultured islets tested on day 18 (p<0.05, vs. control on day 0 and encapsulated islets on day 18). The decreased insulin storage/secretion ability of the control islets was also shown by decreased insulin staining by dithizone (DTZ) on day 18 (FIG. 4C). To further assess beta cell function, dynamic glucose stimulated insulin release was tested in a perifusion system using islets that were cultured with or without hydrogel encapsulation for 18 days. Although the same number of islets was present in both the encapsulated and control samples on day 0, islets in the control group disintegrated over time and did not show stimulated insulin secretion. In contrast, encapsulated islets responded well to glucose stimulation (FIG. 4D).

Hydrogels can also be formed by mixing two different polymers. For example, as presented in FIG. 3A, thiol-terminated pCB-A and pyridyldisulfide-terminated pCB-B were synthesized via a combination of ATRP and click chemistry. The hydrogel can be formed by mixing pCB-A with pCB-B under physiological conditions (see FIG. 3B). Because the hydrogel can be formed under physiological conditions, cells such as stem cells, immune cells, neural cells, hormone-secreting cells, and heart cells can be added in the process of gelation in order to be encapsulated within the hydrogels. In addition, due to the hydrogel is being crosslinked with disulfide bonds, the hydrogel can be degraded by biological agents such as cysteine.

Functionalized Zwitterionic Polymers-Based Hydrogel for Peripheral Blood Stem Cell (PBSC) Cell Encapsulation.

As described above for rat islet cells, peripheral blood stem cell (PBSC) cell were also encapsulated in a representative hydrogel of the invention.

Figure 5A:
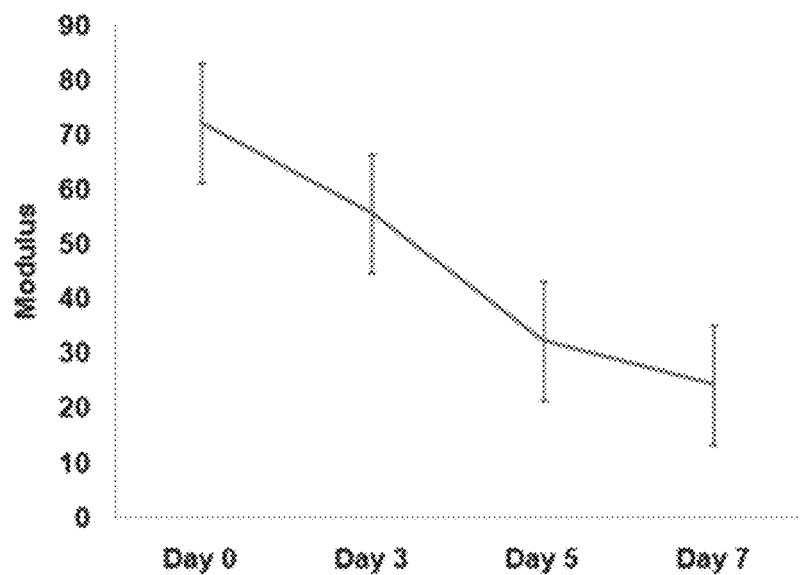
FIGS. 5A and 5B present data for encapsulated peripheral blood stem cell (PBSC) cells cultured in a representative hydrogel (pCB hydrogel) of the invention.
Figure 5B:
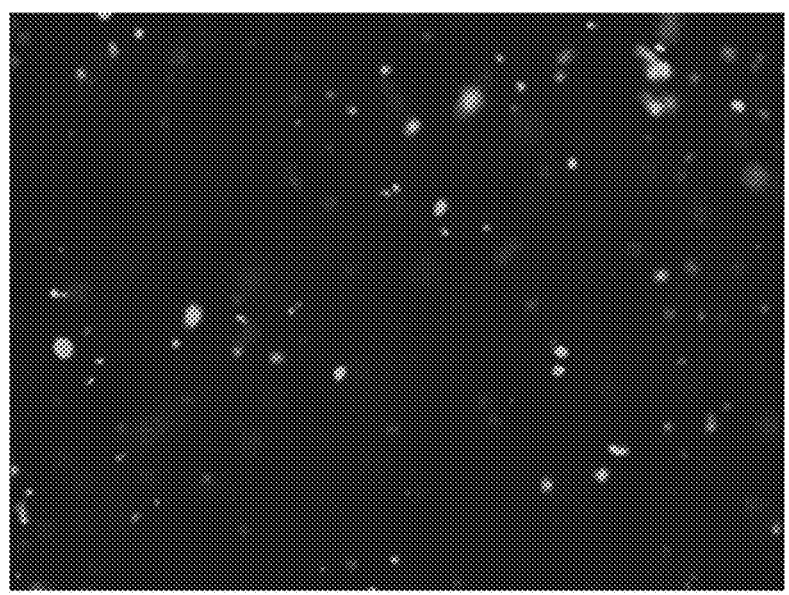

FIGS. 5A and 5B present data for encapsulated peripheral blood stem cell (PBSC) cells cultured in a representative hydrogel (pCB hydrogel) of the invention. FIG. 5A illustrates hydrogel modulus over time (hydrogel degradation). FIG. 5B is an image showing the results of a LIVE/DEAD assay performed on encapsulated PBSC cells within the pCB hydrogels after 7-day in vitro culture.

The hydrogels of the invention can further include components or additives that are advantageously administered by the methods of the invention.

In certain embodiments, the hydrogel further includes cells. In these embodiments, the cells are contained within or encapsulated in the hydrogel. The nature of the cell encapsulated in the hydrogel is not limited (natural cells and genetically modified cells, as well as triturates thereof). Representative cells that are advantageously encapsulated in the hydrogel include exocrine secretory epithelial cells, hormone secreting cells, keratinizing epithelial cells, wet stratified barrier epithelial cells, sensory transducer cells, autonomic neuron cells, sense organ and peripheral neuron supporting cells, neurons and glial cells, lens cells, hepatocytes, adipocytes, lipocytes, barrier function cells, kidney cells, heart cells, extracellular matrix cells, contractile cells, blood and immune system cells such as erythrocytes, monocytes, neutrophils, mast cells, T cells, stem cells, germ cells, nurse cells, interstitial cells, progenitor cells, and hematopoietic stem cells.

In certain embodiments, the hydrogel further includes viruses. In these embodiments, the viruses are contained within or encapsulated in the hydrogel. Representative viruses include retroviruses and adenoviruses.

In certain embodiments, the hydrogel further includes bacteria. In these embodiments, the bacteria are contained within or encapsulated in the hydrogel. Representative bacteria include clostridial species, *S. typhimurium*, and *E. coli*.

Other materials advantageously encapsulated in the hydrogels include proteins, peptides, nucleic acids (oligonucleotides), polysacharrides, small molecules (i.e., organic, inorganic and organometallic compounds having a molecular weight less than about 800 g/mole) and nanomaterials. Representative proteins include antibodies, antibody fragments, enzymes (e.g., therapeutic and protective enzymes), and peptides. Representative nucleic acids include DNAs (e.g., cDNA) and RNAs (e.g., siRNA, mRNA) Representative small molecules include thereapuetic agents and diagnostic agents (e.g., fluorescent and magnetic resonance imaging agetns). Representative nanomaterials include carbon nanostructures (e.g., carbon nanotubes and graphenes) and quantum dots.

Other materials advantageously encapsulated in the hydrogels include lipoplexes, polymerosomes, polyplexes, dendrimers, and inorganic particles.

In certain embodiments, the hydrogel is crosslinked with a degradable crosslinker. Representative degradable crosslinkers include peptides, polysacharrides, anhydride crosslinkers, dissulfide crosslinkers, and polyester crosslinkers. In these embodiments, the hydrogel can be designed to degrade under specific circumstances (e.g., physiological conditions), such as by hydrolysis or digestion by enzymes.

In certain embodiments, the hydrogel of the invention is prepare from functionalized zwitterionic polymers and has formula (J):

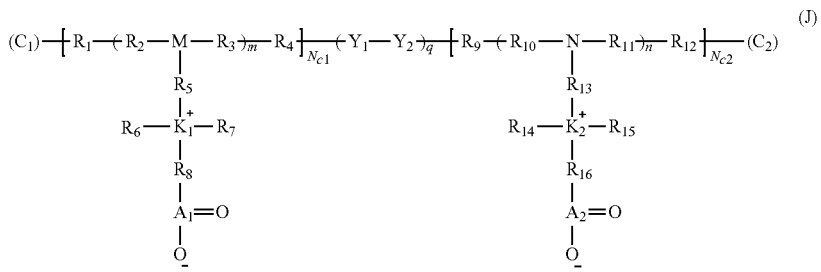

wherein (C1) and (C2) are cores and are independently selected from acrylate functionalized C1-C6 alkyl, and C6-C12 aryl groups; amine functionalized C1-C6 alkyl, and C6-C12 aryl groups; amide functionalized C1-C6 alkyl, and C6-C12 aryl groups; epoxy functionalized C1-C6 alkyl, and C6-C12 aryl groups; C1-C6 alkyl, and C6-C12 aryl groups; or other macromolecular core;

$Y_1$ and $Y_2$ are linking groups and independently selected from —O(CH$_2$)$_n$—, —S(CH$_2$)$_n$—, —C(=O)(CH$_2$)$_n$—, —C(=S)(CH$_2$)$_n$—, —C(=NH)(CH$_2$)$_n$—, —NH(CH$_2$)$_n$—, —(CH$_2$)$_n$C(=O)—, —(CH$_2$)$_n$OC(=O)—, —(CH$_2$)$_n$NHC(=O)—, —(CH$_2$)$_n$NHC(=S)—, —(CH$_2$)$_n$—C(=O)—, —(CH$_2$)$_n$SC(=S)—, —(CH$_2$)$_n$NH—C(=NH)—, —(CH$_2$)C(=O)NHNH—, wherein n is an integer from 1 to 20, and other linkages which can be formed from functional groups X defined above;

$R_1$-$R_8$ are as described above for (A);

$R_9$-$R_{16}$ are as for $R_1$-$R_8$; respectively,

M is as described above for (A);

N is M;

$K_1$ and $K_2$ are independently as described above for K for (A);

$A_1$ is C, SO, SO$_2$, P, or PO$^-$;

$A_2$ is C, SO, SO$_2$, P, or PO$^-$;

m is an integer from 5 to about 10,000;

n is an integer from 5 to about 10,000;

$N_{c1}$ and $N_{c2}$ are core multiplicities and are integers independently selected from 2 to 1000; and q is the an integer intermediate $N_{c1}$ and $N_{c2}$.

In other embodiments, the hydrogel of the invention is prepare from functionalized zwitterionic polymers and has formula (K):

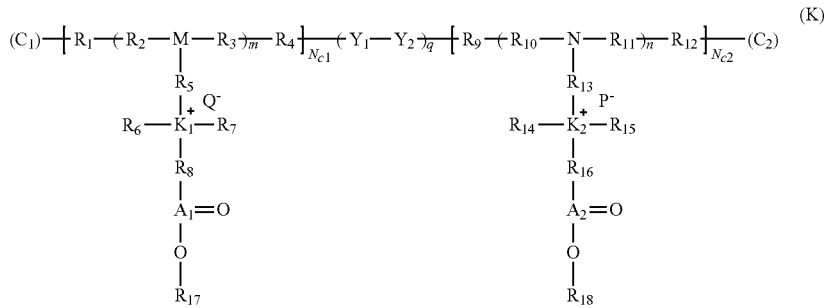

wherein the definitions of the substituents are as described above for (J), P⁻ is as described for Q⁻ for (B), and $R_{17}$ and $R_{18}$ are functional groups and are independently selected from the groups defined by $R_9$ for (B).

In certain embodiments, the hydrogel of the invention is prepare from functionalized mixed charge copolymers and has formula (L):

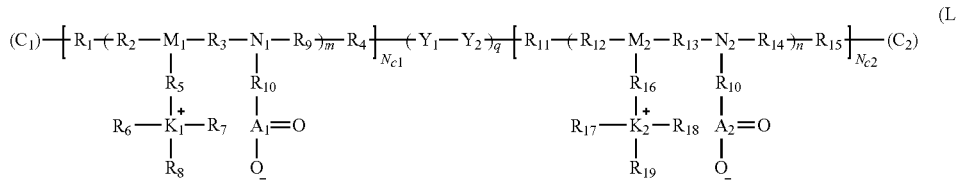

wherein (C1) and (C2) are cores and are independently selected from acrylate functionalized C1-C6 alkyl, and C6-C12 aryl groups; amine functionalized C1-C6 alkyl, and C6-C12 aryl groups; amide functionalized C1-C6 alkyl, and C6-C12 aryl groups; epoxy functionalized C1-C6 alkyl, and C6-C12 aryl groups; C1-C6 alkyl, and C6-C12 aryl groups; or other macromolecular core;

$Y_1$ and $Y_2$ are linking groups and independently selected from —O(CH$_2$)$_n$—, —S(CH$_2$)$_n$—, —C(=O)(CH$_2$)$_n$—, —C(=S)(CH$_2$)$_n$—, —C(=NH)(CH$_2$)$_n$—, —NH(CH$_2$)$_n$—, —(CH$_2$)$_n$C(=O)—, —(CH$_2$)$_n$OC(=O)—, —(CH$_2$)$_n$NHC(=O)—, —(CH$_2$)$_n$NHC(=S)—, —(CH$_2$)$_n$—C(=O)—, —(CH$_2$)$_n$SC(=S)—, —(CH$_2$)$_n$NH—C(=NH)—, —(CH$_2$)C(=O)NHNH—, wherein n is an integer from 1 to 20, and other linkages which can be formed from functional groups X defined above;

$R_1$-$R_{10}$ are as described above for (E);

$R_{11}$-$R_{20}$ are as for counterpart $R_1$-$R_{10}$;

$M_1$ and $M_2$ are independently as described above for M for (K);

$N_1$ and $N_2$ are independently as described above for N for (K);

$K_1$ and $K_2$ are independently as described above for K for (K);

$A_1$ is C, SO, SO$_2$, P, or PO⁻;
$A_2$ is C, SO, SO$_2$, P, or PO⁻;
m is an integer from 5 to about 10,000;
n is an integer from 5 to about 10,000;

$N_{c1}$ and $N_{c2}$ are core multiplicities and are integers independently selected from 2 to 1000; and q is the an integer intermediate $N_{c1}$ and $N_{c2}$.

In other embodiments, the hydrogel of the invention is prepare from functionalized mixed charge copolymers and has formula (M):

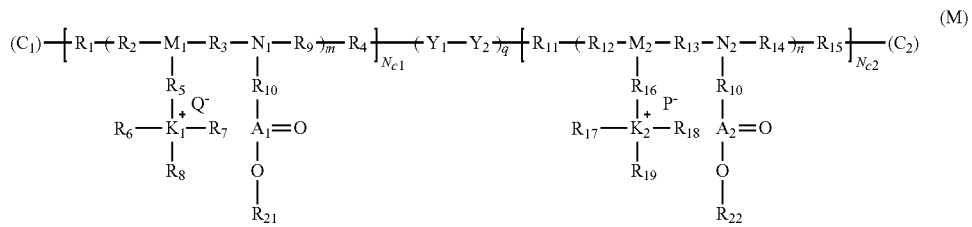

wherein the definitions of the substituents are as described above for (L), P⁻ is as for Q⁻ as described for (F), and $R_{21}$ and $R_{22}$ are functional groups and are independently selected from the groups defined by $R_8$ for (F).

Surfaces Treated with Zwitterionic or Mixed Charge Polymeric Hydrogels

In another aspect, the invention provides surfaces that have been treated with the zwitterionic or mixed charge hydrogels of the invention. The hydrogels of the invention, which in certain embodiments are hydrolyzable to zwitterionic polymers or mixed charge copolymers, can be advantageously used as coatings for the surfaces of a variety of devices including, for example, medical devices.

The hydrogels of the invention are advantageously used to coat surfaces to provide biocompatible, antimicrobial, and nonfouling surfaces. Accordingly, in another aspect, the invention provides devices and materials having a surface (i.e., one or more surfaces) to which have been applied (e.g., coated, covalently coupled, ionically associated, hydrophobically associated) one or more crosslinked zwitterionic hydrogels of the invention. Representative devices and carriers that may be advantageously treated with a hydrogel of the invention, modified to include a hydrogel of the invention, or incorporates a hydrogel of the invention include:

particle (e.g., nanoparticle) having a surface treated with, modified to include, or incorporates a hydrogel of the invention;

drug carrier having a surface treated with, modified to include, or incorporates a material of the invention;

non-viral gene delivery system having a surface treated with, modified to include, or incorporates a hydrogel of the invention;

biosensor having a surface treated with, modified to include, or incorporates a hydrogel of the invention;

devices for bioprocesses or bioseparations, such as membranes for microbial suspension, hormone separation, protein fractionation, cell separation, waste water treatment, oligosaccharide bioreactors, protein ultrafiltration, and diary processing having a surface treated with, modified to include, or incorporates a hydrogel of the invention;

implantable sensor having a surface treated with, modified to include, or incorporates a hydrogel of the invention;

subcutaneous sensor having a surface treated with, modified to include, or incorporates by a hydrogel of the invention;

implant, such as a breast implant, cochlear implant, and dental implant having a surface treated with, modified to include, or incorporates a hydrogel of the invention;

contact lens having a surface treated with, modified to include, or incorporates a hydrogel of the invention;

tissue scaffold having a surface treated with, modified to include, or incorporates a hydrogel of the invention;

implantable medical devices, such as an artificial joint, artificial heart valve, artificial blood vessel, pacemaker, left ventricular assist device (LVAD), artery graft, and stent having a surface treated with, modified to include, or incorporates a hydrogel of the invention; and medical devices, such as an ear drainage tube, feeding tube, glaucoma drainage tube, hydrocephalous shunt, keratoprosthesis, nerve guidance tube, urinary catheter, tissue adhesive, and x-ray guide having a surface treated with, modified to include, or incorporates by a hydrogel of the invention.

Other representative substrates and surfaces that may be advantageously treated with a hydrogel of the invention, modified to include a hydrogel of the invention, or incorporates a hydrogel of the invention include fabrics and such as in clothing (e.g., coats, shirts, pants, undergarments, including such as worn by hospital and military personnel), bedding (e.g., blankets, sheets, pillow cases, mattresses, and pillows), toweling, and wipes.

Other representative substrates and surfaces that may be advantageously treated with a hydrogel of the invention, modified to include a hydrogel of the invention, or incorporates a hydrogel of the invention include working surfaces such as tabletops, desks, and countertops.

The hydrogels of the invention can be coated onto a variety of surfaces including surfaces of objects, devices, and components such as implantable biosensors; wound care devices, glues and selants, a contact lens; a dental implant; an orthopedic device such as an artificial joint, an artificial bone, an artificial ligaments, and an artificial tendon; a cardiovascular device such as a cathether, an artificial valve, an artificial vessel, an artificial stent, LVADs, or and a rhythm management device; gastroenterology devices such as feeding tubes, alimentary canal clips, gastro-intestinal sleeves, or gastric balloons; OB/Gyn devices such as implantable birth control devices or vaginal slings; nephrology devices such as anastomotic connectors or subdermal ports; neurosurgery devices such as nerve guidance tubes, cerebrospinal fluid drains or shunts, dermatology devices such as skin repair devices an ophthalmic device such as a shunt, otorhinolaryngology devices such as stents, cochlear implants, tubes, shunts or spreaders, an intra-ocular lense; an aesthetic implant such as a breast implant, a nasal implant, and a cheek implant; a neurologic implant such as a nerve stimulation device, a cochlear implant, and a nerve conduit; a hormone control implant such as a blood sugar sensor and an insulin pump; an implanted biosensor; an access port device; and a tissue scaffold pulmonic devices such as valves for management of COPD or artificial lungs; radiology devices such as radio-opaque or sono-opaque markers; or urology devices such as catheters or artificial urethrae.

In Situ Zwitterionic and Mixed Charge Polymeric Hydrogels

In a further aspect, the invention provides a method for making a zwitterionic or mixed charge polymeric hydrogel. In certain embodiments, the method is an in situ method, such as an in vivo method, in which a suitably functionalized zwitterionic star polymer or a suitably functionalized mixed charge star copolymer is introduced to an environment where the hydrogel is desirably located. By virtue of the complimentary functional groups of the functionalized zwitterionic star polymer or the functionalized mixed charge star copolymer, the polymers or copolymers are crosslinked to provide the hydrogel in situ.

When the environment is an in vivo location, the functionalized zwitterionic star polymer or a functionalized mixed charge star copolymer can be introduced to the desired site by, for example, injection.

By this method the hydrogel and its added cargo can be advantageously formed at desired in vivo sites.

In certain embodiments, two suitable functionalized zwitterionic polymers of the invention, each having a functional group of a reactive pair (e.g., the first polymer bearing first functional groups and the second polymer bearing second functional groups, the first and second functional groups being reactive toward one another to covalently couple the first polymer to the second polymer), are administered such that the two polymers react to form a hydrogel when combined or come into contact with each other in situ (e.g., in vivo after injection at the desired site).

In other embodiments, two functionalized mixed charged copolymers of the invention, each having one functional group of a reactive pair (e.g., the first polymer bearing first functional groups and the second polymer bearing second functional groups, the first and second functional groups being reactive toward one another to covalently couple the first polymer to the second polymer), are administered such that the two polymers react to form a hydrogel when combined or come into contact with each other in situ (e.g., in vivo after injection at the desired site).

Zwitterionic and Mixed Charge Star Polymer Therapeutic Agent Conjugates

In another aspect, the invention provides zwitterionic and mixed charge polymers and copolymers having therapeutic agents covalently coupled thereto. These conjugates are useful for therapeutic agent delivery. Controlled release of therapeutic agents from the polymers of the invention by hydrolysis The following is a description of a representative conjugate of the invention and release of therapeutic agent from the conjugate.

Figure 6:
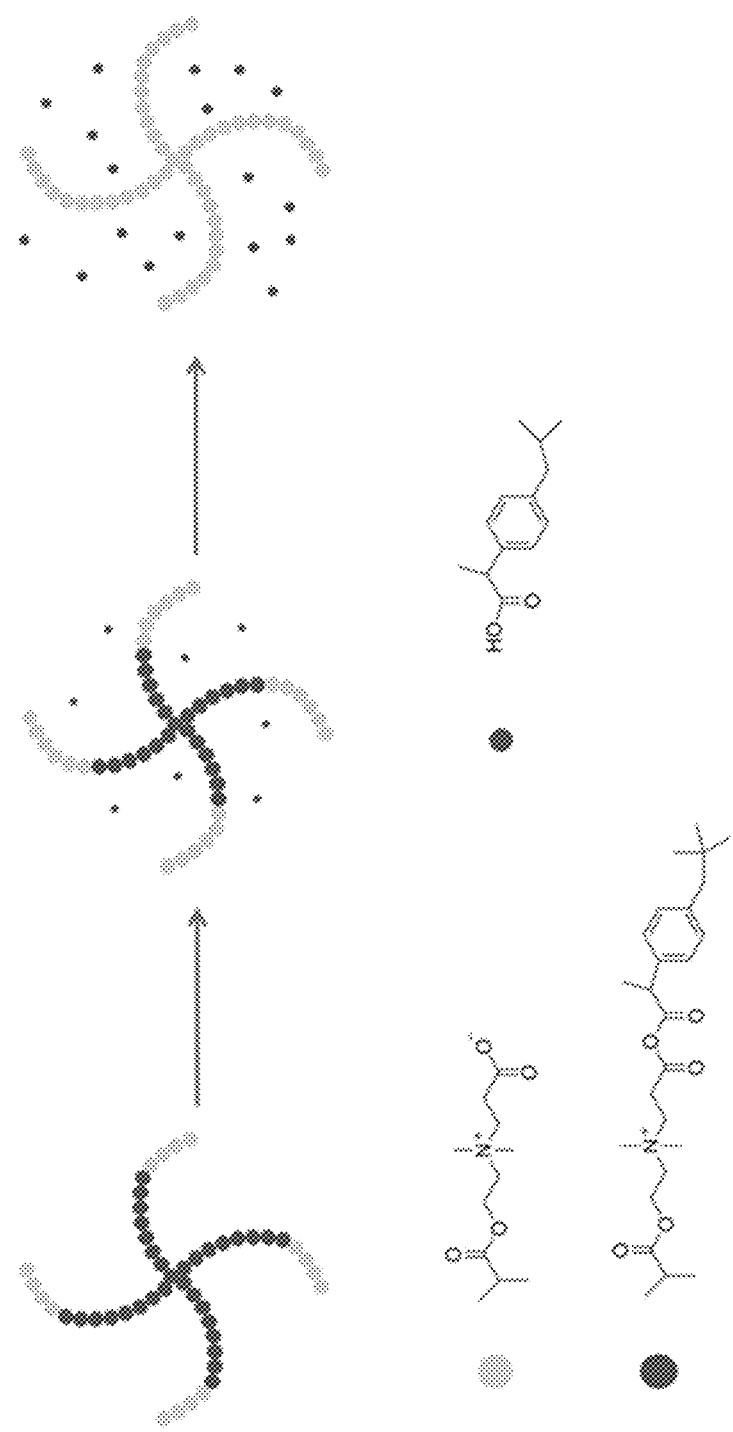
FIG. 6 is a schematic illustration of the release of a representative therapeutic agent from a representative star polymer of the invention having zwitterionic (polycarboxybetaine) branches. The star polymer was prepared by ATRP from the tetrafunctional core having the radical initiator groups and carboxybetaine methacrylate-therapeutic agent monomers (CH$_2$=C(CH$_3$)—C(=O)—CH$_2$CH$_2$—N(CH$_3$)$_2$$^+$—CH$_2$CH$_2$—CO$_2$-therapeutic agent). In the representative star polymer shown, the branches are further extended by extension polymerization with CBMA to provide branches having constitutional units that are zwitterionic in addition to constitutional units bearing the therapeutic agent. The star polymer illustrated in FIG. 6 is a block copolymer. It will be appreciated that in certain embodiments, the star polymer is a random copolymer prepared by copolymerization of zwitterionic monomers (e.g., CBMA) and zwitterionic-therapeutic agent monomers (e.g., CBMA-therapeutic agent). On hydrolysis of the star polymer, the therapeutic agent is released. Hydrolysis of the star polymer and release of the therapeutic agent regenerates a zwitterionic constitutional unit in the star polymer.

FIG. 6 is a schematic illustration of the release of a representative therapeutic agent from a representative star polymer of the invention having zwitterionic (polycarboxybetaine) branches. The star polymer was prepared by ATRP from the tetrafunctional core having the radical initiator groups and carboxybetaine methacrylate-therapeutic agent monomers ($CH_2=C(CH_3)-C(=O)-CH_2CH_2-N(CH_3)_2{}^+-CH_2CH_2-CO_2$-therapeutic agent). In the representative star polymer shown, the branches are further extended by extension polymerization with CBMA to provide branches having constitutional units that are zwitterionic in addition to constitutional units bearing the therapeutic agent. The star polymer illustrated in FIG. 6 is a block copolymer. It will be appreciated that in certain embodiments, the star polymer is a random copolymer prepared by copolymerization of zwitterionic monomers (e.g., CBMA) and zwitterionic-therapeutic agent monomers (e.g., CBMA-therapeutic agent). On hydrolysis of the star polymer, the therapeutic agent is released. Hydrolysis of the star polymer and release of the therapeutic agent regenerates a zwitterionic constitutional unit in the star polymer. As shown in FIG. 6, the therapeutic agent is ibuprophen, and the monomer for synthesizing the star polymer capable of releasing ibuprophen is prepared by condensation of CBMA with ibuprophen.

As shown in FIG. 6, ibuprofen was incorporated into carboxybetaine methacrylate (CBMA) via anhydride formation reaction by stirring with dicyclohexylcarbodiimide (DCC) in dichloromethane (DCM) to provide a polymerizable monomer. A 4-arm star zwitterionic polymer was prepared from the monomer to provide a polymer therapeutic agent conjugate. As shown in FIG. 6, the therapeutic agent is released by hydrolysis. The resulting polymer after the hydrolysis is converted to its counterpart zwitterionic polymer.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range (i.e., denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value).

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The following examples are presented for the purpose of illustrating, not limiting the invention.

EXAMPLES

Example 1

Representative Hydrogel: First and Second Zwitterionic Polymers Cyclooctyne/Azide Chemistry In this example, a representative hydrogel of the invention is prepared from first and second zwitterionic polymers. The first polymer includes pendant first reactive groups (i.e., cyclooctyne) and the second polymer includes pendant second reactive groups (i.e., azide).

Mixing the two polymers without any external stimuli provides the hydrogel.

The formation of the first and second polycarboxybetaine polymers and the hydrogel formed from the polymers is shown below.

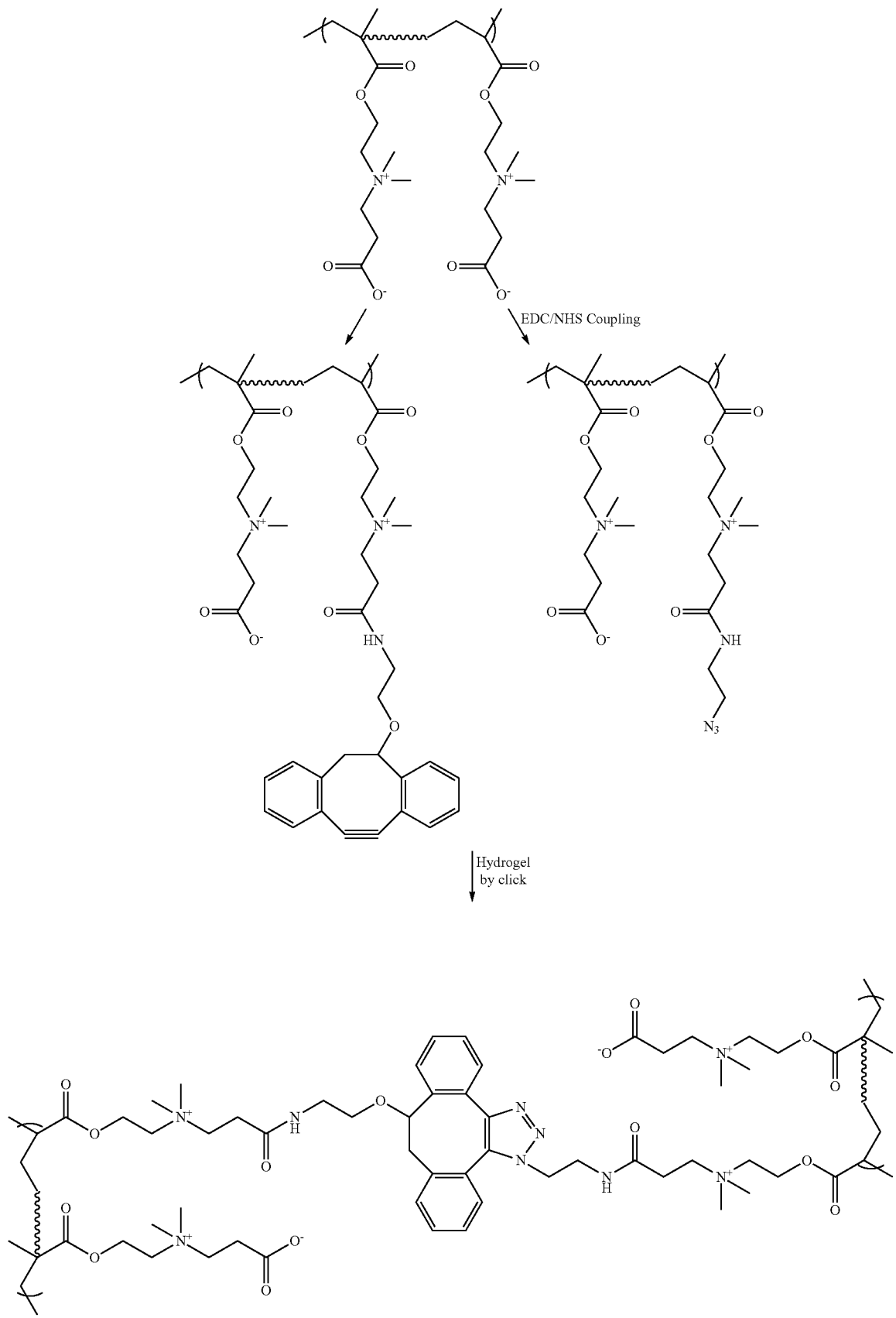

The polycarboxybetaine (pCB) polymer is functionalized in two different reactions with a cyclooctyne amine and an azido amine, respectively, using the known EDC/NHS coupling. The pCB polymers are first activated by EDC/NHS chemistry and then the polymer is purified by precipitation in THF. The activated polymer is then treated with respective amines. The polymer is again purified by precipitation in THF. The purified polymer is dried under vacuum. The degree of functionalization is characterized by $^1$H and $^{13}$C NMR. These two functionalized pCB polymers are mixed and then undergo the click reaction to form the hydrogel. The extent of functionalization and hence the extent of crosslinking can be easily varied by changing the amount of reactive amines.

Example 2

Functionalized Zwitterionic Copolymers

In this example, the preparation of a representative functionalized zwitterionic copolymer of the invention is described. The representative functionalized copolymer includes pendant groups (i.e., N-hydroxysuccinimide groups) that allow for covalent coupling of further activating groups (complimentary reactive groups) to provide crosslinkable polymers useful for forming hydrogels of the invention.

Carboxybetaine methacrylate monomer (CBMA) is functionalized with N-hydroxysuccinimide (NHS-CBMA). This monomer is copolymerized with carboxybetaine methacrylate monomer (CBMA) (see FIG. 11). The resultant polymer is a random polymer of CBMA and NHS-CBMA. The copolymerization is shown below.

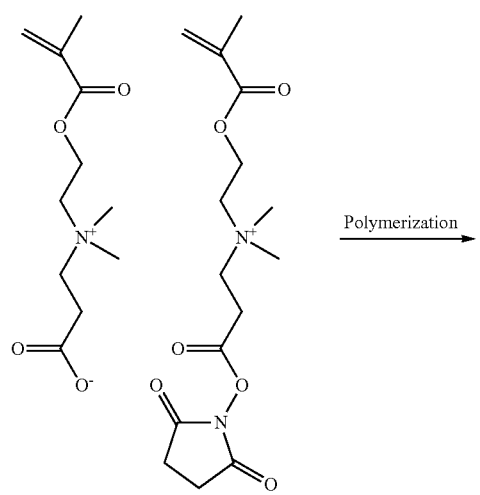

Polymerization →

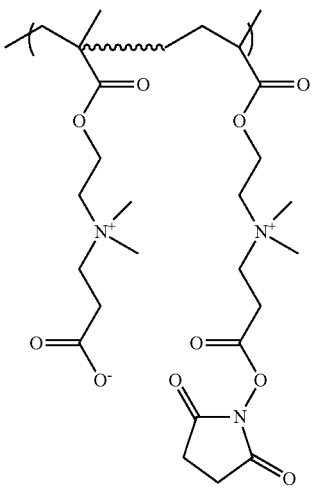

-continued

The feed ratio of the two monomers can be varied to provide functionalized polymers having different degrees of functionalization. The activated polymer can be readily further functionalized with suitable amines, facilitating steps 1a and 1b in FIG. 9

An NHS activated carboxybetaine monomer is synthesized first. This monomer is polymerized along with carboxybetainemethacrylate at different feed ratios. The polymer obtained is already activated. This polymer is purified by precipitating in THF to remove all the small molecular impurities (e.g., unreacted monomers, initiators) and then vacuum dried. The polymer is characterized using $^1$H and $^{13}$C NMR.

Example 3

Representative Hydrogel: First and Second Zwitterionic Polymers Thiol/Maleimide Chemistry In this example, a representative hydrogel of the invention is prepared from first and second zwitterionic polymers. The first polymer includes pendant first reactive groups (i.e., thiol) and the second polymer includes pendant second reactive groups (i.e., maleimide).

The formation of the first and second polycarboxybetaine polymers is shown below.

The synthesis of a random copolymer of carboxybetaine methacrylate and maleimide functionalized CBMA monomer is shown below.

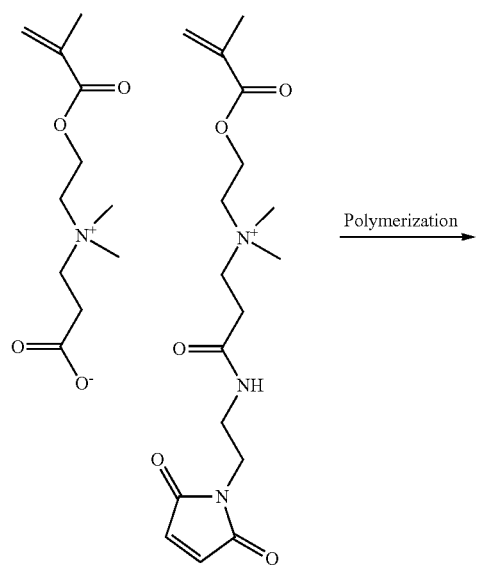

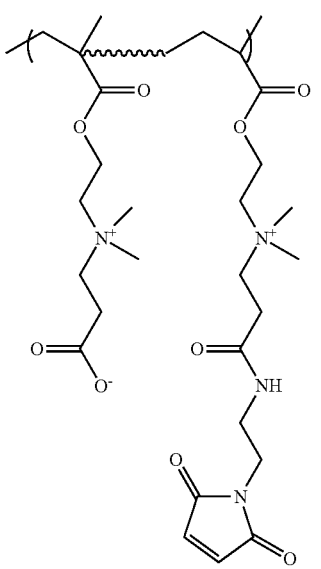

The synthesis of a random copolymer of carboxybetaine methacrylate and ethanethiol functionalized CBMA monomer is shown below.

Mixing the two polymers without any external stimuli provides the hydrogel.

A functionalized carboxybetaine monomer is synthesized first with complimentary clickable groups. This functionalized monomer is random polymerized with CBMA monomer. As representative examples, maleimide and thiol functionalized CBMA monomers are synthesized using amines based on maleimide and thiol. The polymer is purified by precipitation in THF to remove unreacted monomers. The composition of the polymer is confirmed by NMR ($^1$H and $^{13}$C). The amount of functionalized units in the polymer is varied by adjusting the feed ratios. Thus complimentary clickable polymers are synthesized. These polymers are mixed at 5-10 wt % in water to form the hydrogel.

Example 4

Representative Zwitterionic Copolymer: Thiol Pendant Group

In this example, a modified carboxybetaine monomer is synthesized by modification of the ammonium moiety retaining the negative charge on the carboxylate to provide a thiol-functionalized zwitterionic monomer.

Copolymerization of the CBMA and the modified CBMA monomers to provide a functionalized zwitterionic copolymer is shown below.

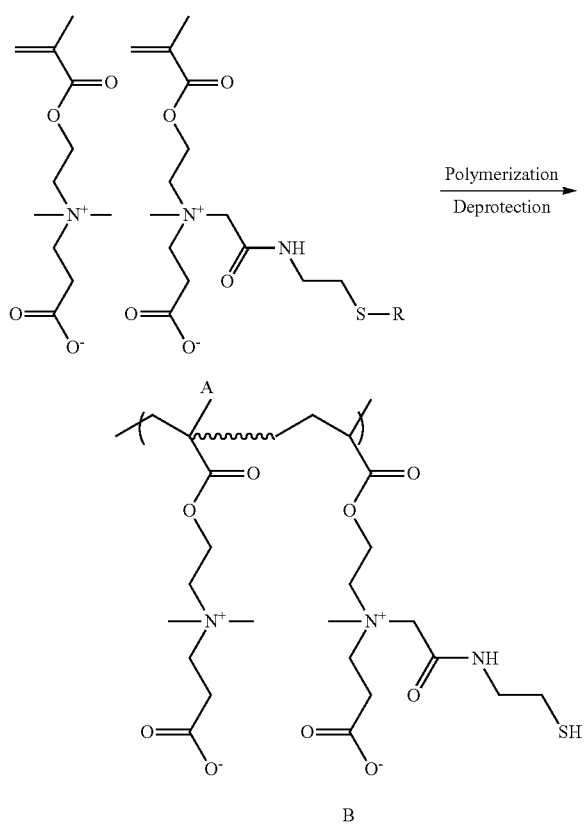

Such a monomer has advantages for high crosslinking rates. A similar monomer and copolymer can be obtained for the corresponding click group counterpart to complete the procedure shown in FIG. 10.

Example 5

Representative Zwitterionic Copolymer Hydrogels: Islets Encapsulation

In this example, islets encapsulation using representative zwitterionic polymers is described.

Functionalized star-shaped pCB polymers were synthesized via a combination of ATRP and 'Click' reaction. Maleimide and thiol group-terminated pCB polymers with different molecular weights were synthesized. pCB hydrogels were formed by mixing maleimide-terminated pCB (pCB-A) with thiol-terminated pCB (pCB-B) together under physiological conditions. The mechanical properties, equilibrium water content (EWC) and pore sizes of the hydrogel can be tuned by adjusting the molecular weight of the polymers and the amount of used polymers.

Synthesis of Star pCB Polymer Via ATRP.

CBMA, 2,2'-bipyridine (bpy), catalysts, tetrafunctional initiator, pentaerythritol tetrakis(2-bromoisobutyrate) were placed in a 10 mL reaction tube, and the mixture was subjected to three freeze-pump-thaw cycles. The mixture stayed under room temperature for 20 min, and water and methanol were added at a 1:1 ratio. The reaction was allowed to continue at room temperature under stirring for 8 h. The polymer product was recovered after treatment with alumina, and finally purified by precipitation twice into acetone. The molecular weight of the polymer can be tuned by the stoichiometric ratio between the monomer and the initiator. Star polymers with weight average molecular weights of 5000, 20000 and 50000 were synthesized. Other living polymerization method such as reversible addition-fragmentation chain-transfer (RAFT) can also be applied to synthesize the polymer.

Synthesis of Functionalized Star pCB Polymers Via Click Chemistry.

After purification, the terminal bromine groups of the star pCB was transformed into azido groups by a nucleophilic substitution reaction with sodium azide in water. The product was purified by dialysis. Lyophilization was used to remove the water. pCB-$N_3$ chains were then reacted with the alkyne-containing compounds in methanol with CuBr/PMDETA as catalyst to produce the star pCB polymers with 4 arm numbers. Thiol terminated star-shaped pCB (pCB-A) and maleimide terminated star-shaped pCB (pCB-B) were obtained after purification via dialysis and lyophilization.

Islets-Free Assessment of the Gelling Properties.

pCB gels were formed by adding pCB-A with various polymer weight percentage solutions of pCB-B in PBS at 37° C. See, e.g., FIG. 3. The hydrogels obtained were washed thoroughly with distilled water to remove the unreacted polymers. The EWCs of the hydrogels were measured at 37° C. using a gravimetric method. The temperature was controlled by a thermostatic water bath with a precision of +0.1° C. The samples were immersed in 0.1 M PBS buffer solutions (pH 7.4) for at least 24 h and then taken out, blotted with wet filter paper to remove water on the surface, and weighed on a microbalance. After crosslinking, hydrogels were allowed to freely swell in PBS for 24 hours.

In Vitro Islet Function Assessment in pCB Hydrogel.

The biocompatibility of pCB hydrogels was tested in vitro. The viability and the function of the encapsulated porcine islets within pCB hydrogels were tested. In addition, the inhibitory effect of pCB hydrogels on the activation of the complement system, lymphocytes, monocytes, platelets and PMNs and cytokine production were tested.

Islet Viability Assessment.

The viability of porcine islets was quantitatively monitored by luminescence intensity. Hydrogel-encapsulated islets or control islets isolated from pigs (100 islets/well) were cultured for up to 28 days and luminescence intensity was measured using the Xenogen image system (Caliper Life Sciences, Hopkinton, Mass.) by adding 0.75 mg/mL D-luciferin to the islet culture medium. Islet viability was also qualitatively assessed using Live/Dead staining at desired time points. Live/Dead staining was done by incubating cell-laden hydrogels in PBS containing 0.24 mM fluorescein diacetate and 7.5 mM propidium iodide for 10 min. Hydrogels were then rinsed in PBS and imaged by fluorescence microscopy (Olympus IX50, Olympus America, Central Valley, Pa.).

Glucose Consumption During Islet Culture.

Culture media was collected every 48 h during medium exchange, and monitored for glucose level with a One Touch glucose meter (LifeScan, Milpitas, Calif.) in duplicate and averaged. Control medium (Ct) without islets were used as control for each time point. Differences (C0–I0) in the medium glucose level with (I0) and without (C0) islets in the first 48 h are set as baseline cell glucose consumption for each sample. Subsequent changes in glucose levels in samples with islets (It) are calculated as: Percent glucose uptake=(Ct–It)*100/(C0–I0).

Long-Term Response to Glucose Stimulated Insulin and C-Peptide Release.

Islets cultured with or without hydrogel as described above were hand-picked after 14 days in culture and collected in micro-tubes (single islet/tube, sexplicate), washed with RPMI 1640 medium containing 3 mM glucose (low-glucose media) supplemented with 5% FBS 3 times. Islets were cultured in a non-tissue culture coated 96 well plate with either low-glucose or high-glucose (17 mM glucose) media for 16 h at which time concentrations of insulin and C-peptide in supernatant media were measured using Porcine Insulin and Porcine C-peptide Elisa kits (Mercodia, Winston Salem, N.C.) according to the manufacturer's instructions.

Short-Term Response to Glucose Stimulated Insulin Release by Perifusion Assay.

Islets were cultured with or without hydrogel as previously described (200 islets/sample on day 0). On day 28, islets were collected and sandwiched-trapped between a bi-layer of microbeads (Biorad, Hercules, Calif.) in a mini-column and perifused at 37° C. with Krebse Ringer's buffer for 45 min, followed by a low-glucose buffer (3 mM glucose) for 10 min, a high-glucose (17 mM glucose) buffer for 15 min, and finally a low-glucose buffer. Effluents were collected every 2 min starting from the first 3 mM medium. The medium samples or effluents collected in the experiment was analyzed for insulin concentration using an Enzyme-Linked ImmunoSorbent Assay (ELISA) kit (Mercodia, Winston Salem, N.C.) for porcine insulin following the manufacturer's protocol.

Example 6

Representative Zwitterionic Copolymer Hydrogels: T Cell Encapsulation

Figure 7:
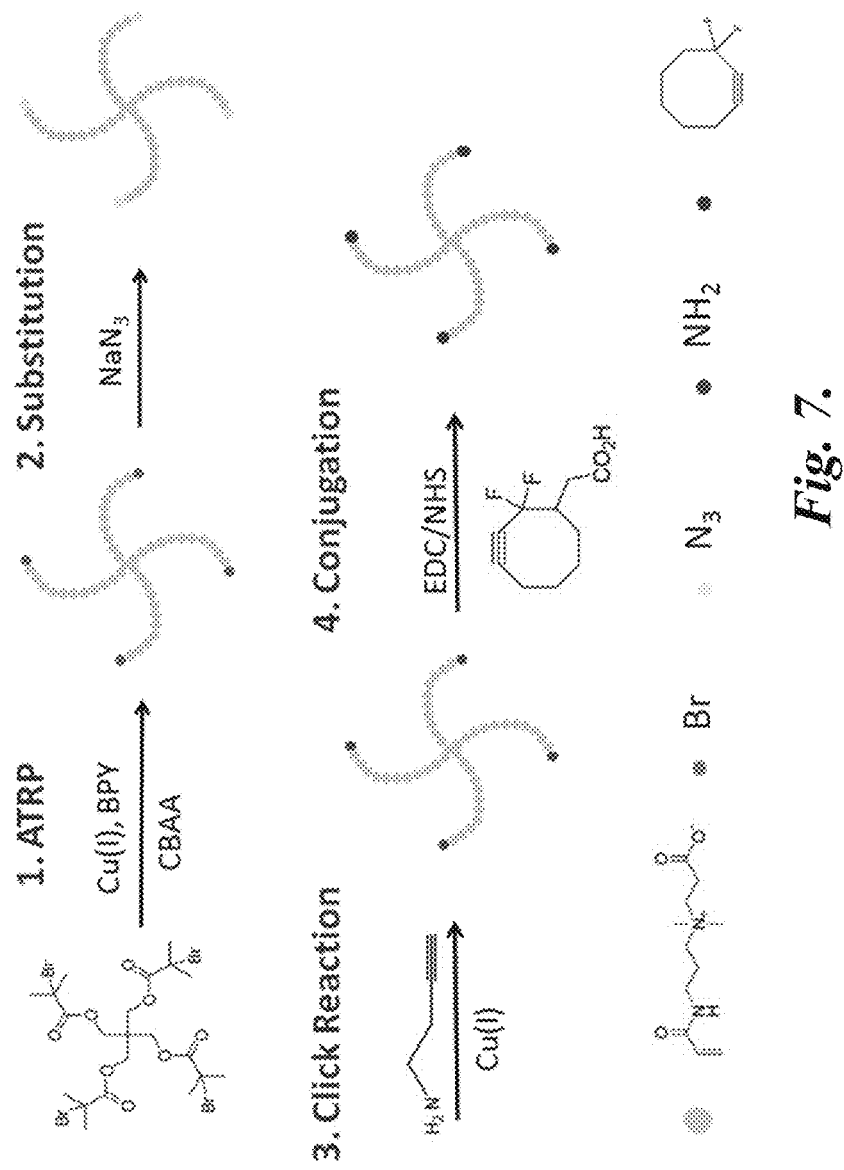
FIG. 7 is a schematic illustration of the preparation of a representative star pCB of the invention useful for making hydrogels for cell encapsulation.

Functionalized star-shaped pCB polymers were synthesized via a combination of ATRP, "'click" reaction, and conjugation. The synthesis is illustrated schematically in FIG. 7.

Difluorinated cyclooctyne moiety (DIFO3)-terminated pCB polymers with different molecular weights were synthesized. pCB hydrogels were formed by mixing difluorinated cyclooctyne moiety-terminated pCB (pCB-A) with biodegradable azide-GG-$(KE)_{20}$-GPQGIWGQ-$(KE)_{20}$-GG-azide together under physiological conditions. The mechanical properties, equilibrium water content (EWC), and pore sizes of the hydrogel can be tuned by adjusting the molecular weight of the polymers and the amount of used polymers.

Synthesis of Star pCB Polymer Via ATRP.

CBMA, 2,2'-bipyridine (bpy), catalysts, tetrafunctional initiator, pentaerythritoltetrakis(2-bromoisobutyrate) were placed in a 10 mL reaction tube, and the mixture was subjected to three freeze-pump-thaw cycles. The mixture stayed under room temperature for 20 min, and water and methanol were added at a 1:1 ratio. The reaction was allowed to continue at room temperature under stirring for 8 h. The polymer product was recovered after treatment with alumina, and finally purified by precipitation twice into acetone. The molecular weight of the polymer can be tuned by the stoichiometric ratio between the monomer and the initiator. Star polymers with weight average molecular weights of 5000, 20000 and 50000 were synthesized. Other living polymerization method such as reversible addition-fragmentation chain-transfer (RAFT) can also be applied to synthesize the polymer.

Synthesis of Functionalized Star pCB Polymers Via Click Chemistry.

After purification, the terminal bromine groups of the star pCB was transformed into azido groups by a nucleophilic substitution reaction with sodium azide in water. The product was purified by dialysis. Lyophilization was used to remove the water. pCB-$N_3$ chains were then reacted with the alkyne-$NH_2$ compounds in methanol with CuBr/PMDETA as catalyst to produce the star pCB polymers with 4 arm numbers. Amine-terminated star-shaped pCB was obtained after purification via dialysis and lyophilization. Obtained polymer was further reacted with DIFO3 via EDC/NHS reaction and the resulted polymer was obtained after purification via dialysis and lyophilization.

Assessment of the Hydrogel Gelling Properties.

pCB gels were formed by adding DIFO3-terminated pCB with various polymer weight percentage solutions of aforementioned peptide in PBS at 37° C. The hydrogels obtained were washed thoroughly with distilled water to remove the unreacted polymers. The EWCs of the hydrogels were measured at 37° C. using a gravimetric method. The temperature was controlled by a thermostatic water bath with a precision of ±0.1° C. The samples were immersed in 0.1 M PBS buffer solutions (pH 7.4) for at least 24 h and then taken out, blotted with wet filter paper to remove water on the surface, and weighed on a microbalance. After crosslinking, hydrogels were allowed to freely swell in PBS for 24 hours.

In Vitro T Cell Encapsulation and Viability Test in pCB Hydrogel.

Figure 8:
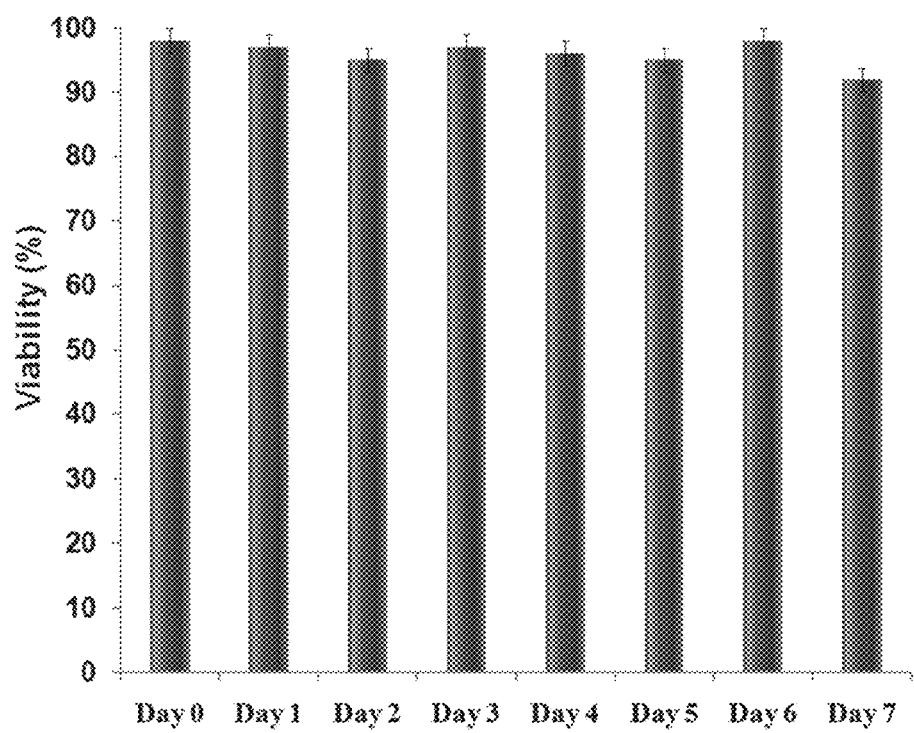
FIG. 8 is compares viability of T cells encapsulated within representative pCB hydrogels of the invention.

The biocompatibility of pCB hydrogels was tested in vitro. Human peripheral blood $CD4^+CD45RA^+$ T Cells were added into the mixed solution in the process of gelation. The T cell encapsulating hydrogel was placed and cultured in RPMI 1640 Medium+10% fetal bovine serum. After 7 days culture, the hydrogel was dissolved by MMP protein and the cells were harvested by centrifuge. The viability of the encapsulated T cells within pCB hydrogels were tested via trypan blue. Almost 100% viability were found in the whole culture process (see FIG. 8).

While illustrative embodiments have been illustrated and described, it will be appreciated that various changes can be made therein without departing from the spirit and scope of the invention.

The invention claimed is:

1. A hydrogel, comprising a first polymer covalently coupled to a second polymer,
    wherein the first polymer comprises a first core having two or more polymeric branches covalently coupled to and extending from the first core, wherein the polymeric branches covalently coupled to and extending from the first core comprise first constitutional units selected from the group consisting of zwitterionic constitutional units and mixed charge constitutional units, and wherein the two or more polymeric branches covalently coupled to and extending from the first core each comprise one or more first functional groups effective for covalently coupling the first polymer to the second polymer,
    wherein the second polymer comprises a second core having two or more polymeric branches covalently coupled to and extending from the second core, wherein the polymeric branches covalently coupled to and extending from the second core comprise second constitutional units selected from the group consisting of zwitterionic constitutional units and mixed charge constitutional units, and wherein the two or more polymeric branches covalently coupled to and extending from the second core each comprise one or more second functional groups effective for covalently coupling the second polymer to the first polymer;
    wherein the hydrogel comprises covalent bonds linking the first polymer and the second polymer formed by reaction of the one or more first functional groups and the one or more second functional groups; and wherein the one or more first functional groups and the one or more second functional groups are selected from an azide and an alkyne, an azide and an alkene, a thiol and a maleimide, or a thiol and a disulfide.

2. A hydrogel, comprising a first polymer covalently coupled to a second polymer, wherein the first polymer comprises a first core having two or more polymeric branches covalently coupled to and extending from the first core, wherein the polymeric branches covalently coupled to and extending from the first core comprise first constitutional units selected from the group consisting of zwitterionic constitutional units and mixed charge constitutional units, and wherein the two or more polymeric branches covalently coupled to and extending from the first core each comprise one or more first functional groups effective for covalently coupling the first polymer to the second polymer, wherein the second polymer comprises a second core having two or more polymeric branches covalently coupled to and extending from the second core, wherein the polymeric branches covalently coupled to and extending from the second core comprise second constitutional units selected from the group consisting of zwitterionic constitutional units and mixed charge constitutional units, and wherein the two or more polymeric branches covalently coupled to and extending from the second core each comprise one or more second functional groups effective for covalently coupling the second polymer to the first polymer;

wherein the hydrogel comprises covalent bonds linking the first polymer and the second polymer via a cross-linking agent having two or more third functional groups, wherein the covalent bonds linking the first and second polymers are formed by reaction of the one or more first functional groups and the two or more third functional groups and the one or more second functional groups and the two or more third functional groups, and wherein the one or more first functional groups and the one or more second functional groups are independently selected from an azide, alkyne, alkene, thiol, maleimide, or disulfide.

3. The hydrogel of claim 2, wherein the one or more first functional group is a thiol, the one or more second functional group is a thiol, and the two or more third functional groups are a thiol or a disulfide.

4. The hydrogel of claim 2, wherein the one or more first functional groups and two or more third functional groups are selected from an azide and an alkyne, an azide and an alkene, a thiol and a maleimide, or a thiol and a disulfide.

5. The hydrogel of claim 2, wherein the one or more second functional groups and two or more third functional groups are selected from an azide and an alkyne, an azide and an alkene, a thiol and a maleimide, or a thiol and a disulfide.

6. The hydrogel of claim 1, wherein the first constitutional units are zwitterionic constitutional units.

7. The hydrogel of claim 1, wherein the first constitutional units are mixed charge constitutional units.

8. The hydrogel of claim 1, wherein the one or more first functional groups are positioned at the terminus of the polymeric branches covalently coupled to and extending from the first core.

9. The hydrogel of claim 1, wherein the one or more first functional groups are positioned along the backbone of the polymeric branches covalently coupled to and extending from the first core.

10. The hydrogel of claim 1, wherein the one or more of the first constitutional units comprise the one or more first functional groups.

11. The hydrogel claim 1, wherein the second constitutional units are zwitterionic constitutional units.

12. The hydrogel of claim 1, wherein the second constitutional units are mixed charge constitutional units.

13. The hydrogel of claim 1, wherein the one or more second functional groups are positioned at the terminus of the polymeric branches covalently coupled to and extending from the second core.

14. The hydrogel of claim 1, wherein the one or more second functional groups are positioned along the backbone of the polymeric branches covalently coupled to and extending from the second core.

15. The hydrogel of claim 1, wherein the one or more of the second constitutional units comprise the one or more second functional groups.

16. The hydrogel of claim 1, wherein the one or more first functional groups and the one or more second functional groups are the same.

17. The hydrogel of claim 1, wherein the one or more first functional groups and the one or more second functional groups are different.

18. The hydrogel of claim 1 further comprising cells, viruses, bacteria, or components thereof, or genetically altered variants thereof.

19. The hydrogel of claim 18, wherein the cells are exocrine secretory epithelial cells, hormone secreting cells, keratinizing epithelial cells, wet stratified barrier epithelial cells, sensory transducer cells, autonomic neuron cells, sense organ cells, peripheral neuron supporting cells, neurons, glial cells, lens cells, hepatocytes, adipocytes, lipocytes, barrier function cells, kidney cells, heart cells, extracellular matrix cells, contractile cells, blood cells, immune system cells, erythrocytes, monocytes, neutrophils, mast cells, T cells, stem cells, germ cells, nurse cells, interstitial cells, progenitor cells, or hematopoietic stem cells.

20. The hydrogel of claim 1, wherein the one or more first functional group is a thiol and the one or more second functional group is a thiol, maleimide, or disulfide.

21. The hydrogel of claim 1, wherein the one or more first functional group is an azide and the one or more second functional group an alkyne or an alkene.

22. The hydrogel claim 2, wherein the first constitutional units are zwitterionic constitutional units.

23. The hydrogel of claim 2, wherein the first constitutional units are mixed charge constitutional units.

24. The hydrogel of claim 2, wherein the one or more first functional groups are positioned at the terminus of the polymeric branches covalently coupled to and extending from the first core.

25. The hydrogel of claim 2, wherein the one or more first functional groups are positioned along the backbone of the polymeric branches covalently coupled to and extending from the first core.

26. The hydrogel of claim 2, wherein one or more of the first constitutional units comprise the one or more first functional groups.

27. The hydrogel of claim 2, wherein the second constitutional units are zwitterionic constitutional units.

28. The hydrogel of claim 2, wherein the second constitutional units are mixed charge constitutional units.

29. The hydrogel of claim 2, wherein the one or more second functional groups are positioned at the terminus of the polymeric branches covalently coupled to and extending from the first core.

30. The hydrogel of claim 2, wherein the one or more second functional groups are positioned along the backbone of the polymeric branches covalently coupled to and extending from the first core.

31. The hydrogel of claim 2, wherein the one or more of the second constitutional units comprise the one or more second functional groups.

32. The hydrogel of claim 2, wherein the one or more first and the one or more second functional groups are the same.

33. The hydrogel of claim 2, wherein the one or more first and the one or more second functional groups are different.

34. The hydrogel of claim 2, further comprising cells, viruses, bacteria, or components thereof, or genetically altered variants thereof.

35. The hydrogel of claim 34, wherein the cells are exocrine secretory epithelial cells, hormone secreting cells, keratinizing epithelial cells, wet stratified barrier epithelial cells, sensory transducer cells, autonomic neuron cells, sense organ cells, peripheral neuron supporting cells, neurons, glial cells, lens cells, hepatocytes, adipocytes, lipocytes, barrier function cells, kidney cells, heart cells, extracellular matrix cells, contractile cells, blood cells, immune system cells erythrocytes, monocytes, neutrophils, mast cells, T cells, stem cells, germ cells, nurse cells, interstitial cells, progenitor cells, or hematopoietic stem cells.

* * * * *